(12) United States Patent
Nguyen et al.

(10) Patent No.: US 11,567,580 B2
(45) Date of Patent: Jan. 31, 2023

(54) ADAPTIVE THRESHOLDING AND NOISE REDUCTION FOR RADAR DATA

(71) Applicant: Samsung Electronics Co., Ltd., Suwon-si (KR)

(72) Inventors: Khuong N. Nguyen, Frisco, TX (US); Wenxun Qiu, Allen, TX (US); Vutha Va, Plano, TX (US); Boon Loong Ng, Plano, TX (US)

(73) Assignee: Samsung Electronics Co., Ltd., Suwon-si (KR)

( * ) Notice: Subject to any disclaimer, the term of this patent is extended or adjusted under 35 U.S.C. 154(b) by 46 days.

(21) Appl. No.: 17/158,794

(22) Filed: Jan. 26, 2021

(65) Prior Publication Data
US 2021/0232228 A1    Jul. 29, 2021

Related U.S. Application Data

(60) Provisional application No. 62/967,159, filed on Jan. 29, 2020, provisional application No. 63/064,653, filed on Aug. 12, 2020.

(51) Int. Cl.
| | | |
|---|---|---|
| *G06F 3/01* | (2006.01) | |
| *G06N 3/04* | (2006.01) | |
| *G01S 7/41* | (2006.01) | |

(52) U.S. Cl.
CPC .............. *G06F 3/017* (2013.01); *G01S 7/415* (2013.01); *G01S 7/417* (2013.01); *G06N 3/0445* (2013.01); *G06N 3/0454* (2013.01)

(58) Field of Classification Search
CPC ........... G06F 3/017; G06F 2203/04108; G06F 3/0416; G06F 3/043; G01S 7/415; G01S 7/417; G01S 13/582; G06N 3/0445; G06N 3/0454; G06N 3/0481; G06N 3/08; A61B 5/05; A61B 5/6898; A61B 5/7264;
(Continued)

(56) References Cited

U.S. PATENT DOCUMENTS

| | | |
|---|---|---|
| 9,702,967 B2 | 7/2017 | Luebbert |
| 10,186,030 B2 * | 1/2019 | Park ........................ G06V 10/25 |

(Continued)

FOREIGN PATENT DOCUMENTS

| | | |
|---|---|---|
| CN | 110208785 A | 9/2019 |
| CN | 110221288 A | 9/2019 |

*Primary Examiner* — Grant Sitta

(57) ABSTRACT

An electronic device for gesture recognition, includes a processor operably connected to a transceiver. The transceiver is configured to transmit and receive signals for measuring range and speed. The processor is configured to transmit the signals, via the transceiver. in response to a determination that a triggering event occurred, the processor is configured to track movement of an object relative to the electronic device within a region of interest based on reflections of the signals received by the transceiver to identify range measurements and speed measurements associated with the object. The processor is also configured to identify features from the reflected signals, based on at least one of the range measurements and the speed measurements. The processor is further configured to identify a gesture based in part on the features from the reflected signals. Additionally, the processor is configured to perform an action indicated by the gesture.

25 Claims, 20 Drawing Sheets

(58) Field of Classification Search
CPC .......... A61B 5/7475; A61B 2560/0487; A61B 5/1122; A61B 5/1123; A61B 5/1117
See application file for complete search history.

(56) References Cited

U.S. PATENT DOCUMENTS

| | | | |
|---|---|---|---|
| 10,247,809 B2 * | 4/2019 | Testar | H01Q 21/061 |
| 10,300,370 B1 * | 5/2019 | Amihood | G06F 21/6245 |
| 10,817,070 B2 | 10/2020 | Lien et al. | |
| 2012/0280900 A1 * | 11/2012 | Wang | G06F 3/0488 |
| | | | 345/156 |
| 2015/0077282 A1 * | 3/2015 | Mohamadi | G01S 5/10 |
| | | | 342/450 |
| 2018/0199377 A1 * | 7/2018 | Sanderovich | H04W 74/0816 |
| 2018/0373340 A1 * | 12/2018 | Cheng | G06F 3/017 |
| 2018/0376509 A1 * | 12/2018 | Trotta | G06F 3/017 |
| 2019/0041494 A1 * | 2/2019 | Roger | G01S 13/87 |
| 2019/0087009 A1 * | 3/2019 | Rao | G01S 7/352 |
| 2019/0212436 A1 * | 7/2019 | Baheti | G01S 13/88 |
| 2019/0219687 A1 * | 7/2019 | Baheti | G01S 7/415 |
| 2019/0240535 A1 * | 8/2019 | Santra | A61B 5/742 |
| 2019/0377063 A1 * | 12/2019 | Cho | G01S 13/50 |
| 2020/0003885 A1 | 1/2020 | Choi | |
| 2020/0064445 A1 * | 2/2020 | Amihood | G06F 1/3275 |
| 2020/0284895 A1 | 9/2020 | Das et al. | |
| 2021/0064146 A1 * | 3/2021 | Stern | G06F 3/0346 |

\* cited by examiner

SCRUB

WAVING LEFT-RIGHT

DOUBLE TAP

ADAPTIVE THRESHOLDING AND NOISE REDUCTION FOR RADAR DATA

CROSS-REFERENCE TO RELATED APPLICATIONS AND CLAIM OF PRIORITY

This application claims priority under 35 U.S.C. § 119(e) to U.S. Provisional patent Application No. 62/967,159 filed on Jan. 29, 2020 and U.S. Provisional Patent Application No. 63/064,653 filed on Aug. 12, 2020. The above-identified provisional patent applications are hereby incorporated by reference in their entirety.

TECHNICAL FIELD

This disclosure relates generally to electronic devices. More specifically, this disclosure relates to adaptive thresholding and noise reduction for radar data.

BACKGROUND

The use of mobile computing technology such as a portable electronic device has greatly expanded largely due to usability, convenience, computing power, and the like. One result of the recent technological development is that electronic devices are becoming more compact, while the number of functions and features that a given device can perform is increasing. For example, certain electronic devices not only provide voice call services using a mobile communication network but can also offer radar capabilities. Radar can operate at various frequency bands including, but not limited to, 6-8 GHz, 28 GHz, 39 GHz, 60 GHz, and 77 GHz. Advancements in radar, such as millimeter wave (mmWave) radar enables high resolution radar signals within a predefined range.

Methods for interacting with and controlling computing devices are continually improving in order to conform to more natural approaches. Various types of computing devices utilize graphical user interfaces (GUI) on a display screen to facilitate control by a user. Objects such as text, images, and video are displayed on a screen and the user can employ various instruments to control the computing device such as, a keyboard, a mouse, a touchpad. Many such methods for interacting with and controlling a computing device generally require a user to physically touch the screen or utilizing an instrument such as a keyboard or mouse to provide a quick and precise input. Touching the screen or using particular instrument to interact with an electronic device can be cumbersome.

SUMMARY

This disclosure provides an adaptive thresholding and noise reduction for radar data.

In one embodiment, electronic device is provided. The electronic device includes a transceiver and a processor. The transceiver is configured to transmit and receive signals for measuring range and speed. The processor is configured to transmit the signals, via the transceiver, In response to a determination that a triggering event occurred, the processor is configured to track movement of an object relative to the electronic device within a region of interest based on reflections of the signals received by the transceiver to identify range measurements and speed measurements associated with the object. The processor is also configured to identify features from the reflected signals, based on at least one of the range measurements and the speed measurements. The processor is further configured to identify a gesture based in part on the features from the reflected signals. Additionally, the processor is configured to perform an action indicated by the gesture.

In another embodiment, a method is provided. The method includes transmitting, signals, via a transceiver. In response to a determination that a triggering event occurred, the method includes tracking movement of an object relative to an electronic device within a region of interest based on reflections of the signals received by the transceiver to identify range measurements and speed measurements associated with the object. The method also includes identifying features from the reflected signals, based on at least one of the range measurements and the speed measurements. The method further includes identifying a gesture based in part on the features from the reflected signals. Additionally, the method includes performing an action indicated by the gesture.

In yet another embodiment a non-transitory computer readable medium embodying a computer program is provided. The computer program comprising computer readable program code that, when executed by a processor of an electronic device, causes the processor to: transmit signals, via a transceiver; in response to a determination that a triggering event occurred, track movement of an object relative to the electronic device within a region of interest based on reflections of the signals received by the transceiver to identify range measurements and speed measurements associated with the object; identify features from the reflected signals, based on at least one of the range measurements and the speed measurements; identify a gesture based in part on the features from the reflected signals, and perform an action indicated by the gesture.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system, or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
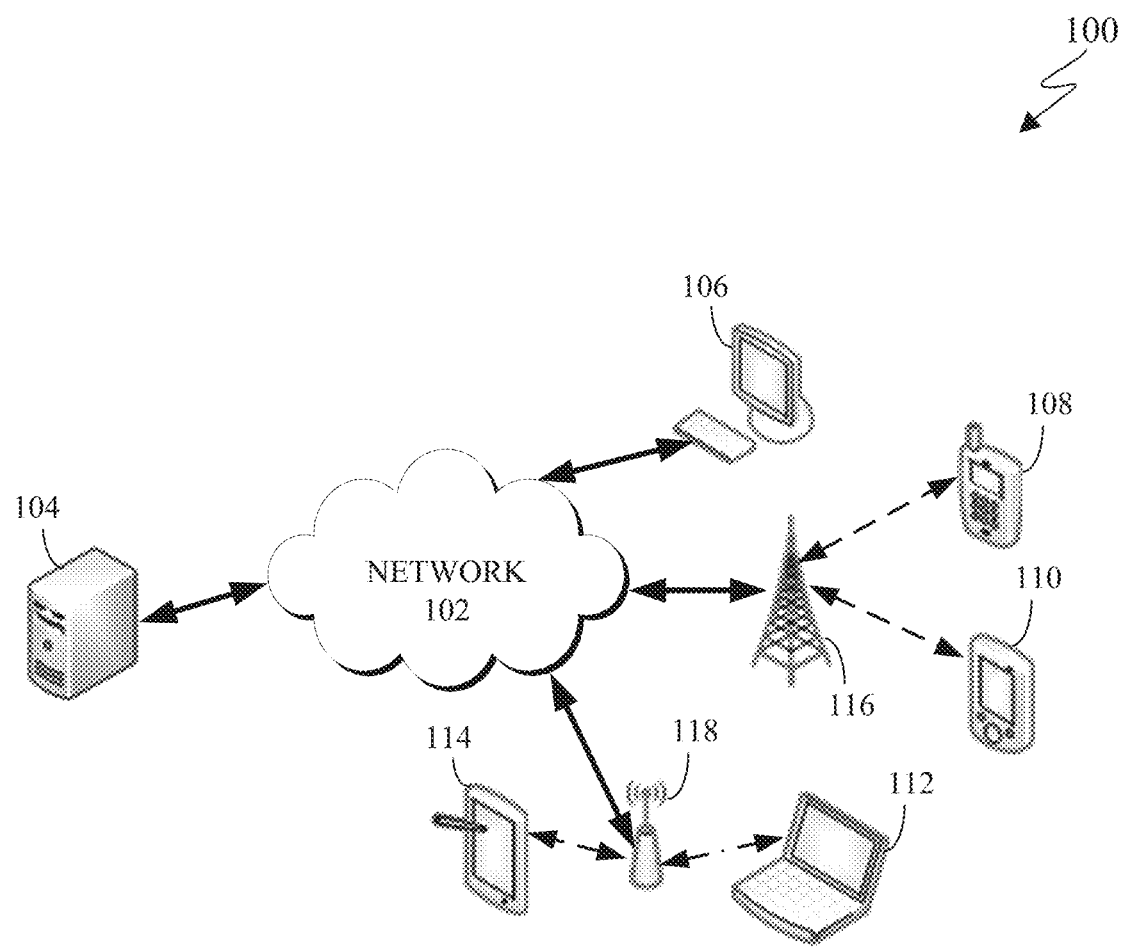
FIG. 1 illustrates an example communication system according to embodiments of this disclosure.

FIGS. 1 through 11, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably-arranged system or device.

An electronic device, according to embodiments of the present disclosure, can include a personal computer (such as a laptop, a desktop), a workstation, a server, a television, an appliance, and the like. In certain embodiments, an electronic device can be a portable electronic device such as a portable communication device (such as a smartphone or mobile phone), a laptop, a tablet, an electronic book reader (such as an e-reader), a personal digital assistants (PDAs), a portable multimedia player (PMP), an MP3 player, a mobile medical device, a virtual reality headset, a portable game console, a camera, and a wearable device, among others. Additionally, the electronic device can be at least one of a part of a piece of furniture or building/structure, an electronic board, an electronic signature receiving device, a projector, or a measurement device. The electronic device is one or a combination of the above-listed devices. Additionally, the electronic device as disclosed herein is not limited to the above-listed devices and can include new electronic devices depending on the development of technology. It is noted that as used herein, the term "user" may denote a human or another device (such as an artificial intelligent electronic device) using the electronic device.

Certain electronic devices include a graphical user interface (GUI) such as a display that allows a user to view information displayed on the display in order to interact with the electronic device. Electronic devices can also include a user input device, such as keyboard, a mouse, a touchpad, a camera, among others. The various types of input devices allow a user to interact with the electronic device. The input devices can be operably connected to the electronic device via a wired or wireless connection. Certain electronic devices can also include a combination of a user input device and a GUI, such as a touch screen. Touch screens allow a user to interact with the electronic device via touching the display screen itself.

Embodiments of the present disclosure recognize and take into consideration that input devices can be cumbersome to use on portable electronic devices since the input devices would need to be carried along with the portable electronic device. Additionally, embodiments of the present disclosure recognize and take into consideration that, the user may be unable to directly touch the input device or a touch screen when the user is unable to reach the electronic device, or uncleaned hands. For example, when the user is wearing gloves, the touch screen may have difficulty detecting the touch input. Similarly, the user may not desire to touch the display of the electronic such as when the hands of the user are dirty or wet.

Accordingly, embodiments of the present disclosure provide user interface mechanisms and methods in which the user can interact with the electronic device while not necessarily touching the electronic device or a user input device that is operably connected to the electronic device. For example, embodiments of the present disclosure provide system and methods for gesture recognition. A gesture refers to detected movements of an external object that is used to control the electronic device. For example, a gesture can be the detected movement of a body part of the user, such as the hand or fingers of a user, which is used to control the electronic device (without the user touching the device or an input device).

For instance, a user can move one finger up and down along or near the edge of an electronic device to increase and decrease the volume. A user can move one finger towards and away from the electronic device to control (increase or decrease) the volume. A user can move one finger up and down along or near the edge of an electronic device to increase and decrease the brightness. A user can move one finger towards and away from the electronic device to control (increase or decrease) the brightness. A user can move one finger up and down along the edge of an electronic device to zoom in and out respectively.

In addition to gesture recognition, embodiments of the present disclosure can also be used for other types of detection. For example, embodiments of the present disclosure can also be used for liveness detection. Liveness detection detects whether an object that is being tracked is alive or inanimate. One such application is vital signal detection. Being able to measure vital signal in a nonintrusive manner can be applied to many scenarios such as heart sensing or mood detection without the need of hooking any device to the person that can cause discomfort to the user. Another related application is for detecting fall-event such as for senior care. Detecting fall event could be done by analyzing the velocity sequence of the tracked user (rather than a gesture). It is noted that for detecting a fall event, the electronic device can use ultra-wideband (UWB) radar, since UWB uses a low carrier frequency which results better propagation properties that can identify situations through a wall and other common materials.

Embodiments of the present disclosure provide methods and an apparatus for gesture recognition. For example, the electronic device as used herein can include an ultrasonic sensor that can both transmit and receive signals. For instance, the electronic device can transmit and receive signals, via the ultrasonic sensor, for range (distance) and speed detection of an object. For another example, the electronic device as used herein can include a transceiver that can both transmit and receive signals. For instance, the electronic device can transmit and receive signals in the similar to radar signals for range (distance) and speed detection of an object. Additionally, embodiments of the present disclosure utilize 802.11ay radar for gesture recognition which concurrently supports both network functions as well as gesture recognition through radar.

While the descriptions of the embodiments of the present discloser, describe a radar based system for gesture recognition, the embodiments can be applied to any other radar based and non-radar based recognition systems. That is, the embodiments of the present disclosure are not restricted to radar and can be applied to other types of sensors that can provide both range and speed measurements. It is noted that when applying the embodiments of the present disclosure using a different type of sensor (a sensor other than a radar transceiver), various components may need to be tuned accordingly.

In certain embodiments, an electronic device can track a finger movements with high resolution in order to control the electronic device without the need to touch the device. For example, the electronic device can track the movement of an object, such as a finger using a millimeter wave (mmWave) radar sensor. A mmWave is able to generate high resolution radar signal within short ranges. It is noted that this disclosure can also be applied to other radar systems operating at other frequency or wavelength.

Embodiments of the present disclosure recognize and take into consideration that that in gesture recognition, identifying an unintentional gesture can inadvertently instruct the electronic device to perform an unintended action. As such, embodiments of the present disclosure provide systems and methods to track small objects (such as the hand or a finger(s) of a user) as well as remove noise from a detected gestures in order to identify the gesture and perform an action indicated by the gesture.

Additionally, embodiments of the present disclosure recognize and take into consideration that raw sensing data collected from radar sensor usually cannot be used directly for gesture recognition because the raw sensing data often includes large amount of irrelevant information. Therefore, embodiments of the present disclosure provide methods for processing the raw sensing data. For example, embodiments of the present disclosure describe identifying certain thresholds and removing noise on a Time Velocity Diagram (TVD) signal produced from a radar sensor.

FIG. 1 illustrates an example communication system 100 in accordance with an embodiment of this disclosure. The embodiment of the communication system 100 shown in FIG. 1 is for illustration only. Other embodiments of the communication system 100 can be used without departing from the scope of this disclosure.

The communication system 100 includes a network 102 that facilitates communication between various components in the communication system 100. For example, the network 102 can communicate IP packets, frame relay frames, Asynchronous Transfer Mode (ATM) cells, or other information between network addresses. The network 102 includes one or more local area networks (LANs), metropolitan area networks (MANs), wide area networks (WANs), all or a portion of a global network such as the Internet, or any other communication system or systems at one or more locations.

In this example, the network 102 facilitates communications between a server 104 and various client devices 106-114. The client devices 106-114 may be, for example, a smartphone, a tablet computer, a laptop, a personal computer, a wearable device, a head mounted display, or the like. The server 104 can represent one or more servers. Each server 104 includes any suitable computing or processing device that can provide computing services for one or more client devices, such as the client devices 106-114. Each server 104 could, for example, include one or more processing devices, one or more memories storing instructions and data, and one or more network interfaces facilitating communication over the network 102.

In certain embodiments, the server 104 is a neural network that is configured to extract features from images or radar signatures for gesture recognition purposes. In certain embodiments, a neural network is included within any of the client devices 106-114. When a neural network is included in a client device, the client device can user the neural network to extract features from images or radar signatures for gesture recognition purposes, without having to transmit content over the network 102. Similarly, when a neural network is included in a client device, the client device can user the neural network to identify the gesture.

Each of the client devices 106-114 represent any suitable computing or processing device that interacts with at least one server (such as the server 104) or other computing device(s) over the network 102. The client devices 106-114 include a desktop computer 106, a mobile telephone or mobile device 108 (such as a smartphone), a PDA 110, a laptop computer 112, and a tablet computer 114. However, any other or additional client devices could be used in the communication system 100. Smartphones represent a class of mobile devices 108 that are handheld devices with mobile operating systems and integrated mobile broadband cellular network connections for voice, short message service (SMS), and Internet data communications. In certain embodiments, any of the client devices 106-114 can emit and collect radar signals via a measuring (or radar) transceiver.

In this example, some client devices 108-114 communicate indirectly with the network 102. For example, the mobile device 108 and PDA 110 communicate via one or more base stations 116, such as cellular base stations or eNodeBs (eNBs). Also, the laptop computer 112 and the tablet computer 114 communicate via one or more wireless access points 118, such as IEEE 802.11 wireless access points. Note that these are for illustration only and that each of the client devices 106-114 could communicate directly with the network 102 or indirectly with the network 102 via any suitable intermediate device(s) or network(s). In certain embodiments, any of the client devices 106-114 transmit information securely and efficiently to another device, such as, for example, the server 104.

Although FIG. 1 illustrates one example of a communication system 100, various changes can be made to FIG. 1. For example, the communication system 100 could include any number of each component in any suitable arrangement. In general, computing and communication systems come in a wide variety of configurations, and FIG. 1 does not limit the scope of this disclosure to any particular configuration. While FIG. 1 illustrates one operational environment in which various features disclosed in this patent document can be used, these features could be used in any other suitable system.

Figure 2:
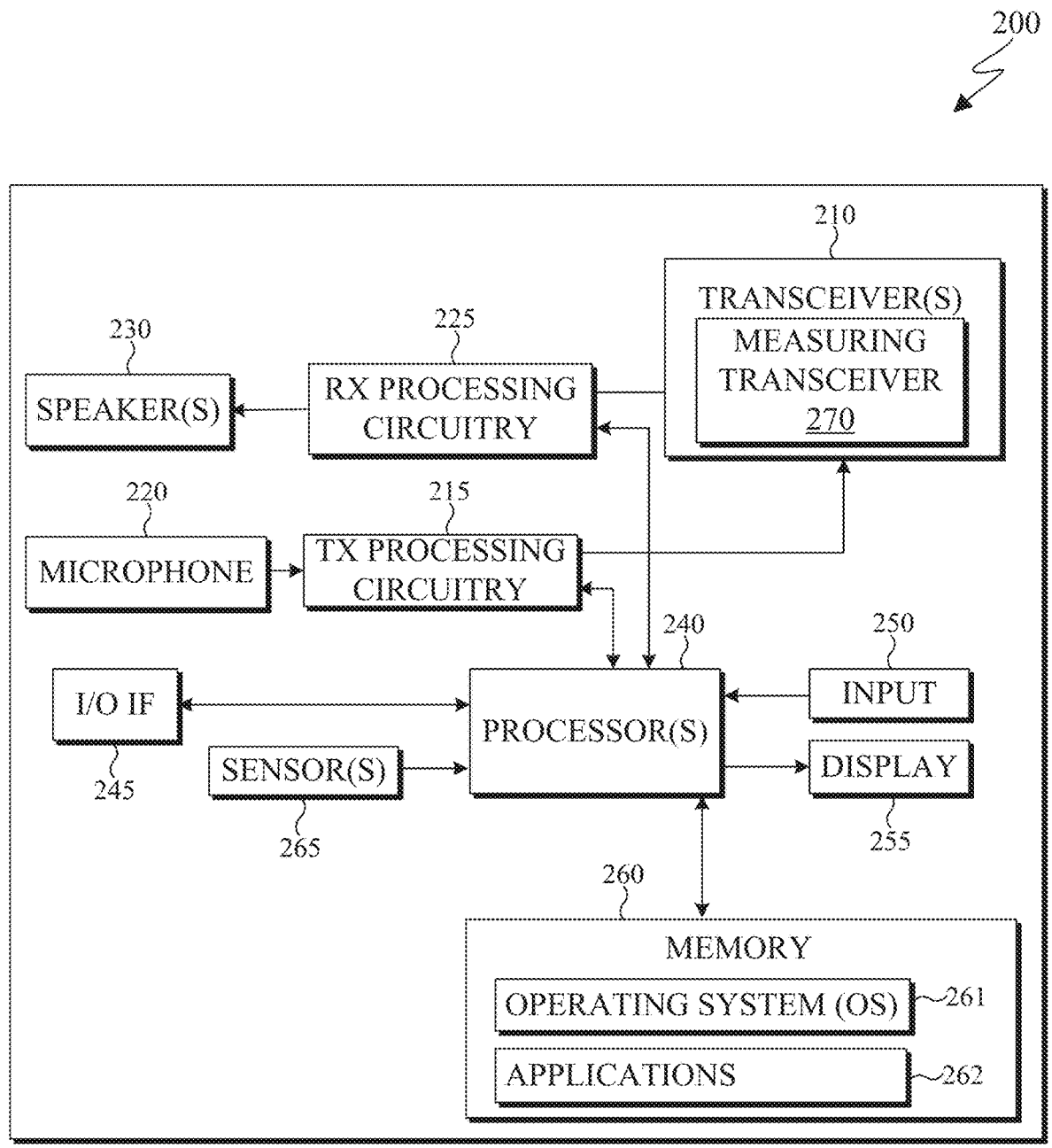
FIG. 2 illustrates an example electronic device according to embodiments of this disclosure.

FIG. 2 illustrates an example electronic device in accordance with an embodiment of this disclosure. In particular, FIG. 2 illustrates an example electronic device 200, and the electronic device 200 could represent the server 104 or one or more of the client devices 106-114 in FIG. 1. The electronic device 200 can be a mobile communication device, such as, for example, a mobile station, a subscriber station, a wireless terminal, a desktop computer (similar to the desktop computer 106 of FIG. 1), a portable electronic device (similar to the mobile device 108, the PDA 110, the laptop computer 112, or the tablet computer 114 of FIG. 1), a robot, and the like.

As shown in FIG. 2, the electronic device 200 includes transceiver(s) 210, transmit (TX) processing circuitry 215, a microphone 220, and receive (RX) processing circuitry 225. The transceiver(s) 210 can include, for example, a RF transceiver, a BLUETOOTH transceiver, a WiFi transceiver, a ZIGBEE transceiver, an infrared transceiver, and various other wireless communication signals. The electronic device 200 also includes a speaker 230, a processor 240, an input/output (I/O) interface (IF) 245, an input 250, a display 255, a memory 260, and a sensor 265. The memory 260 includes an operating system (OS) 261, and one or more applications 262.

The transceiver(s) 210 can include an antenna array including numerous antennas. The antennas of the antenna array can include a radiating element composed of a conductive material or a conductive pattern formed in or on a substrate. The transceiver(s) 210 transmit and receive a signal or power to or from the electronic device 200. The transceiver(s) 210 receives an incoming signal transmitted from an access point (such as a base station, WiFi router, or BLUETOOTH device) or other device of the network 102 (such as a WiFi, BLUETOOTH, cellular, 5G, LTE, LTE-A, WiMAX, or any other type of wireless network). The transceiver(s) 210 down-converts the incoming RF signal to generate an intermediate frequency or baseband signal. The intermediate frequency or baseband signal is sent to the RX processing circuitry 225 that generates a processed baseband signal by filtering, decoding, and/or digitizing the baseband or intermediate frequency signal. The RX processing circuitry 225 transmits the processed baseband signal to the speaker 230 (such as for voice data) or to the processor 240 for further processing (such as for web browsing data).

The TX processing circuitry 215 receives analog or digital voice data from the microphone 220 or other outgoing baseband data from the processor 240. The outgoing baseband data can include web data, e-mail, or interactive video game data. The TX processing circuitry 215 encodes, multiplexes, and/or digitizes the outgoing baseband data to generate a processed baseband or intermediate frequency signal. The transceiver(s) 210 receives the outgoing processed baseband or intermediate frequency signal from the TX processing circuitry 215 and up-converts the baseband or intermediate frequency signal to a signal that is transmitted.

The processor 240 can include one or more processors or other processing devices. The processor 240 can execute instructions that are stored in the memory 260, such as the OS 261 in order to control the overall operation of the electronic device 200. For example, the processor 240 could control the reception of forward channel signals and the transmission of reverse channel signals by the transceiver(s) 210, the RX processing circuitry 225, and the TX processing circuitry 215 in accordance with well-known principles. The processor 240 can include any suitable number(s) and type(s) of processors or other devices in any suitable arrangement. For example, in certain embodiments, the processor 240 includes at least one microprocessor or microcontroller. Example types of processor 240 include microprocessors, microcontrollers, digital signal processors, field programmable gate arrays, application specific integrated circuits, and discrete circuitry. In certain embodiments, the processor 240 can include a neural network.

The processor 240 is also capable of executing other processes and programs resident in the memory 260, such as operations that receive and store data. The processor 240 can move data into or out of the memory 260 as required by an executing process. In certain embodiments, the processor 240 is configured to execute the one or more applications 262 based on the OS 261 or in response to signals received from external source(s) or an operator. Example, applications 262 can include a multimedia player (such as a music player or a video player), a phone calling application, a virtual personal assistant, and the like.

The processor 240 is also coupled to the I/O interface 245 that provides the electronic device 200 with the ability to connect to other devices, such as client devices 106-114. The I/O interface 245 is the communication path between these accessories and the processor 240.

The processor 240 is also coupled to the input 250 and the display 255. The operator of the electronic device 200 can use the input 250 to enter data or inputs into the electronic device 200. The input 250 can be a keyboard, touchscreen, mouse, track ball, voice input, or other device capable of acting as a user interface to allow a user in interact with the electronic device 200. For example, the input 250 can include voice recognition processing, thereby allowing a user to input a voice command. In another example, the input 250 can include a touch panel, a (digital) pen sensor, a key, or an ultrasonic input device. The touch panel can recognize, for example, a touch input in at least one scheme, such as a capacitive scheme, a pressure sensitive scheme, an infrared scheme, or an ultrasonic scheme. The input 250 can be associated with the sensor(s) 265, the measuring transceiver 270, a camera, and the like, which provide additional inputs to the processor 240. The input 250 can also include a control circuit. In the capacitive scheme, the input 250 can recognize touch or proximity.

The display 255 can be a liquid crystal display (LCD), light-emitting diode (LED) display, organic LED (OLED), active matrix OLED (AMOLED), or other display capable of rendering text and/or graphics, such as from websites, videos, games, images, and the like. The display 255 can be a singular display screen or multiple display screens capable of creating a stereoscopic display. In certain embodiments, the display 255 is a heads-up display (HUD).

The memory 260 is coupled to the processor 240. Part of the memory 260 could include a RAM, and another part of the memory 260 could include a Flash memory or other ROM. The memory 260 can include persistent storage (not shown) that represents any structure(s) capable of storing and facilitating retrieval of information (such as data, program code, and/or other suitable information). The memory 260 can contain one or more components or devices supporting longer-term storage of data, such as a read only memory, hard drive, Flash memory, or optical disc.

The electronic device 200 further includes one or more sensors 265 that can meter a physical quantity or detect an activation state of the electronic device 200 and convert metered or detected information into an electrical signal. For example, the sensor 265 can include one or more buttons for touch input, a camera, a gesture sensor, optical sensors, cameras, one or more inertial measurement units (IMUs), such as a gyroscope or gyro sensor, and an accelerometer. The sensor 265 can also include an air pressure sensor, a magnetic sensor or magnetometer, a grip sensor, a proximity sensor, an ambient light sensor, a bio-physical sensor, a temperature/humidity sensor, an illumination sensor, an Ultraviolet (UV) sensor, an Electromyography (EMG) sensor, an Electroencephalogram (EEG) sensor, an Electrocardiogram (ECG) sensor, an IR sensor, an ultrasound sensor, an iris sensor, a fingerprint sensor, a color sensor (such as a Red Green Blue (RGB) sensor), and the like. The sensor 265 can further include control circuits for controlling any of the sensors included therein. Any of these sensor(s) 265 may be located within the electronic device 200 or within a secondary device operably connected to the electronic device 200.

In this embodiment, one of the one or more transceivers in the transceiver 210 is a measuring transceiver 270 that is configured to transmit and receive signals for detecting and ranging purposes. The measuring transceiver 270 can transmit and receive signals for measuring range and speed of an object that is external to the electronic device 200. For example, the measuring transceiver 270 can transmit one or more signals that when reflected off of a moving object and received by the measuring transceiver 270 can be used for determining the range and speed of the object.

The measuring transceiver 270 may be any type of transceiver including, but not limited to a WiFi transceiver, for example, an 802.11ay transceiver. In certain embodiments, the measuring transceiver 270 includes a radar sensor. For example, the measuring transceiver 270 can operate both radar and communication signals concurrently. The measuring transceiver 270 includes one or more antenna arrays, or antenna pairs, that each includes a transmitter (or transmitter antenna) and a receiver (or receiver antenna 159). The measuring transceiver 270 can transmit signals at a various frequencies. For example, the measuring transceiver 270 can transmit signals at frequencies including, but not limited to, 6 GHz, 7 GHz, 8 GHz, 28 GHz, 39 GHz, 60 GHz, and 77 GHz. In some embodiments, the signals transmitted by the measuring transceiver 270 can include, but are not limited to, mmWave signals. The measuring transceiver 270 can receive the signals, which were originally transmitted from the measuring transceiver 270, after the signals have bounced or reflected off of target objects in the surrounding environment of the electronic device 200.

Figure 4A:
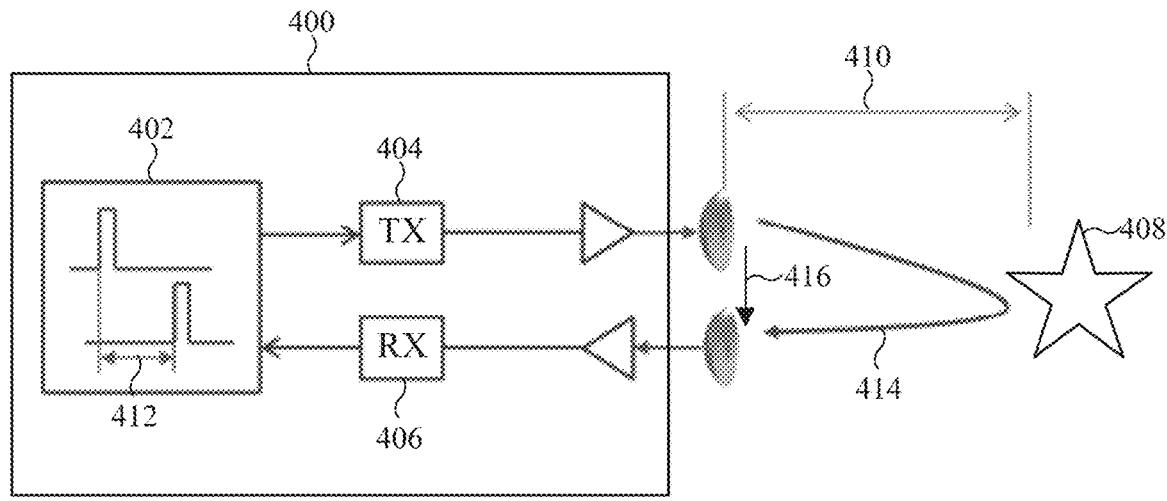
FIG. 4A illustrates an example architecture of a monostatic radar signal according to embodiments of this disclosure.

In certain embodiments, the measuring transceiver 270 is a monostatic radar transmitter and receiver which are positioned at the same or similar location. For example, the transmitter and the receiver can use the same antenna or nearly-co-located while using separate, but adjacent antennas. Monostatic radars are assumed coherent, i.e. transmitter and receiver are synchronized via a common time reference. FIG. 4A, below, illustrates an example monostatic radar.

The transmitter, of the measuring transceiver 270, can transmit mmWave signals. The receiver, of the measuring transceiver, can receive the mmWave signals originally transmitted from the transmitter after the mmWave signals have bounced or reflected off of target objects in the surrounding environment of the electronic device 200. The processor 240 can analyze the time difference between when the mmWave signals are transmitted and received to measure the distance of the target objects from the electronic device 200. Based on the time differences, the processor 240 can generate an image of the objection by mapping the various distances.

In certain embodiments, the measuring transceiver 270 is a sensor that can detect range and speed of an object. For example, the measuring transceiver 270 can be a radar-like sensor, an ultrasonic sensor, or the like.

Although FIG. 2 illustrates one example of electronic device 200, various changes can be made to FIG. 2. For example, various components in FIG. 2 can be combined, further subdivided, or omitted and additional components can be added according to particular needs. As a particular example, the processor 240 can be divided into multiple processors, such as one or more central processing units (CPUs), one or more graphics processing units (GPUs), one or more neural networks, and the like. Also, while FIG. 2 illustrates the electronic device 200 configured as a mobile telephone, tablet, or smartphone, the electronic device 200 can be configured to operate as other types of mobile or stationary devices.

Figure 3:
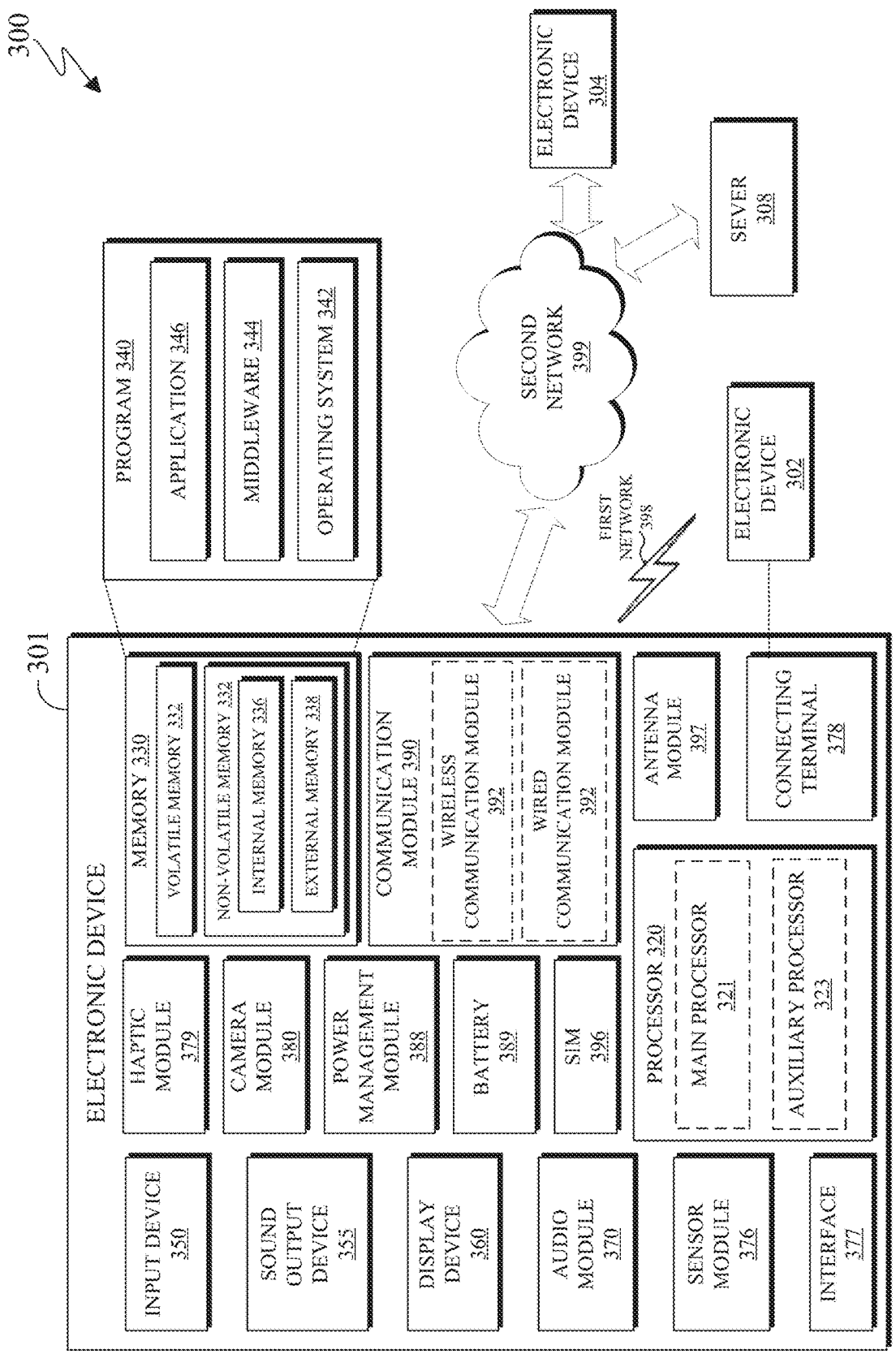
FIG. 3 illustrates an example network configuration according to embodiments of the present disclosure.

FIG. 3 illustrates an example network configuration according to embodiments of the present disclosure. An embodiment of the network configuration shown in FIG. 3 is for illustration only. One or more of the components illustrated in FIG. 3 can be implemented in specialized circuitry configured to perform the noted functions or one or more of the components can be implemented by one or more processors executing instructions to perform the noted functions.

FIG. 3 illustrated a block diagram illustrating a network configuration including an electronic device 301 in a network environment 300 according to various embodiments. As illustrated in FIG. 300, the electronic device 301 in the network environment 300 may communicate with an electronic device 302 via a first network 398 (e.g., a short-range wireless communication network), or an electronic device 304 or a server 308 via a second network 399 (e.g., a long-range wireless communication network). The first network 398 and/or the second network 399 can be similar to the network 102 of FIG. 1. The electronic devices 301, 302, and 304 can be similar to any of the client devices 106-114 of FIG. 1 and include similar components to that of the electronic device 200 of FIG. 2. The server 308 can be similar to the server 104 of FIG. 1.

The electronic device 301 can be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

According to an embodiment, the electronic device 301 may communicate with the electronic device 304 via the server 308. According to an embodiment, the electronic device 301 may include a processor 320, memory 330, an input device 350, a sound output device 355, a display device 360, an audio module 370, a sensor module 376, an interface 377, a haptic module 379, a camera module 380, a power management module 388, a battery 389, a communication module 390, a subscriber identification module (SIM) 396, or an antenna module 397. In some embodiments, at least one (e.g., the display device 360 or the camera module 380) of the components may be omitted from the electronic device 301, or one or more other components may be added in the electronic device 301. In some embodiments, some of the components may be implemented as single integrated circuitry. For example, the sensor module 376 (e.g., a fingerprint sensor, an iris sensor, or an illuminance sensor) may be implemented as embedded in the display device 360 (e.g., a display).

The processor 320 may execute, for example, software (e.g., a program 340) to control at least one other component (e.g., a hardware or software component) of the electronic device 301 coupled with the processor 320 and may perform various data processing or computation. According to one embodiment, as at least part of the data processing or computation, the processor 320 may load a command or data received from another component (e.g., the sensor module 376 or the communication module 390) in volatile memory 332, process the command or the data stored in the volatile memory 332, and store resulting data in non-volatile memory 334.

According to an embodiment, the processor 320 may include a main processor 321 (e.g., a central processing unit (CPU) or an application processor (AP)), and an auxiliary processor 323 (e.g., a graphics processing unit (GPU), an image signal processor (ISP), a sensor hub processor, or a communication processor (CP)) that is operable independently from, or in conjunction with, the main processor 321. Additionally or alternatively, the auxiliary processor 323 may be adapted to consume less power than the main processor 321, or to be specific to a specified function. The auxiliary processor 323 may be implemented as separate from, or as part of the main processor 321.

The auxiliary processor 323 may control at least some of functions or states related to at least one component (e.g., the display device 360, the sensor module 376, or the communication module 390) among the components of the electronic device 301, instead of the main processor 321 while the main processor 321 is in an inactive (e.g., sleep) state, or together with the main processor 321 while the main processor 321 is in an active state (e.g., executing an application). According to an embodiment, the auxiliary processor 323 (e.g., an image signal processor or a communication processor) may be implemented as part of another component (e.g., the camera module 380 or the communication module 390) functionally related to the auxiliary processor 323.

The memory 330 may store various data used by at least one component (e.g., the processor 320 or the sensor module 376) of the electronic device 301. The various data may include, for example, software (e.g., the program 340) and input data or output data for a command related thereto. The memory 330 may include the volatile memory 332 or the non-volatile memory 334.

The program 340 may be stored in the memory 330 as software. The program 340 may include, for example, an operating system (OS) 342, middleware 344, or an application 346.

The input device 350 may receive a command or data to be used by other components (e.g., the processor 320) of the electronic device 301, from the outside (e.g., a user) of the electronic device 301. The input device 350 may include, for example, a microphone, a mouse, a keyboard, or a digital pen (e.g., a stylus pen).

In certain embodiments, the input device 350 can include a sensor for gesture recognition. For example, the input device 350 can include a transceiver similar to the measuring transceiver of FIG. 2.

The sound output device 355 may output sound signals to the outside of the electronic device 301. The sound output device 355 may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device 360 may visually provide information to the outside (e.g., a user) of the electronic device 301. The display device 360 may include, for example, a display, a hologram device, or a projector and control circuitry to control a corresponding one of the display, hologram device, or projector. According to an embodiment, the display device 360 may include touch circuitry adapted to detect a touch, or sensor circuitry (e.g., a pressure sensor) adapted to measure the intensity of force incurred by the touch. The display device 360 can be similar to the display 255 of FIG. 2.

The audio module 370 may convert a sound into an electrical signal and vice versa. According to an embodiment, the audio module 370 may obtain the sound via the input device 350, output the sound via the sound output device 355, or output the sound via a headphone of an external electronic device (e.g., an electronic device 302) directly (e.g., wiredly) or wirelessly coupled with the electronic device 301.

The sensor module 376 may detect an operational state (e.g., power or temperature) of the electronic device 301 or an environmental state (e.g., a state of a user) external to the electronic device 301, and then generate an electrical signal or data value corresponding to the detected state. According to an embodiment, the sensor module 376 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor. The sensor module 376 can be similar to the sensors 265 of FIG. 2.

The interface 377 may support one or more specified protocols to be used for the electronic device 101 to be coupled with the external electronic device (e.g., the electronic device 302) directly (e.g., wiredly) or wirelessly. According to an embodiment, the interface 377 may include, for example, a high definition multimedia interface (HDMI), a universal serial bus (USB) interface, a secure digital (SD) card interface, or an audio interface.

A connecting terminal 378 may include a connector via which the electronic device 301 may be physically connected with the external electronic device (e.g., the electronic device 302). According to an embodiment, the connecting terminal 378 may include, for example, a HDMI connector, a USB connector, a SD card connector, or an audio connector (e.g., a headphone connector).

The haptic module 379 may convert an electrical signal into a mechanical stimulus (e.g., a vibration or a movement) or electrical stimulus which may be recognized by a user via his tactile sensation or kinesthetic sensation. According to an embodiment, the haptic module 379 may include, for example, a motor, a piezoelectric element, or an electric stimulator.

The camera module 380 may capture a still image or moving images. According to an embodiment, the camera module 380 may include one or more lenses, image sensors, image signal processors, or flashes.

The power management module 388 may manage power supplied to the electronic device 301. According to one embodiment, the power management module 388 may be implemented as at least part of, for example, a power management integrated circuit (PMIC).

The battery 389 may supply power to at least one component of the electronic device 301. According to an embodiment, the battery 389 may include, for example, a primary cell which is not rechargeable, a secondary cell which is rechargeable, or a fuel cell.

The communication module 390 may support establishing a direct (e.g., wired) communication channel or a wireless communication channel between the electronic device 301 and the external electronic device (e.g., the electronic device 302, the electronic device 304, or the server 308) and performing communication via the established communication channel. The communication module 390 may include one or more communication processors that are operable independently from the processor 320 (e.g., the application processor (AP)) and supports a direct (e.g., wired) communication or a wireless communication.

According to an embodiment, the communication module 390 may include a wireless communication module 392 (e.g., a cellular communication module, a short-range wireless communication module, or a global navigation satellite system (GNSS) communication module) or a wired communication module 394 (e.g., a local area network (LAN) communication module or a power line communication (PLC) module). A corresponding one of these communication modules may communicate with the external electronic device via the first network 398 (e.g., a short-range communication network, such as BLUETOOTH, wireless-fidelity (Wi-Fi) direct, Ultra-WideBand (UWB), or infrared data association (IrDA)) or the second network 399 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 392 may identify and authenticate the electronic device 301 in a communication network, such as the first network 398 or the second network 399, using subscriber information (e.g., international mobile subscriber identity (IMSI)) stored in the subscriber identification module 396.

The antenna module 397 may transmit or receive a signal or power to or from the outside (e.g., the external electronic device) of the electronic device 301. According to an embodiment, the antenna module 397 may include an antenna including a radiating element composed of a conductive material or a conductive pattern formed in or on a substrate (e.g., PCB).

According to an embodiment, the antenna module 397 may include a plurality of antennas. In such a case, at least one antenna appropriate for a communication scheme used in the communication network, such as the first network 398 or the second network 399, may be selected, for example, by the communication module 390 (e.g., the wireless communication module 392) from the plurality of antennas. The signal or the power may then be transmitted or received between the communication module 390 and the external electronic device via the selected at least one antenna.

According to an embodiment, another component (e.g., a radio frequency integrated circuit (RFIC)) other than the radiating element may be additionally formed as part of the antenna module 397.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 301 and the external electronic device 304 via the server 308 coupled with the second network 399. Each of the electronic devices 302 and 304 may be a device of a same type as, or a different type, from the electronic device 301. According to an embodiment, all or some of operations to be executed at the electronic device 301 may be executed at one or more of the external electronic devices 302, 304, or 308. For example, if the electronic device 301 may perform a function or a service automatically, or in response to a request from a user or another device, the electronic device 301, instead of, or in addition to, executing the function or the service, may request the one or more external electronic devices to perform at least part of the function or the service.

The one or more external electronic devices receiving the request may perform the at least part of the function or the service requested, or an additional function or an additional service related to the request and transfer an outcome of the performing to the electronic device 301. The electronic device 301 may provide the outcome, with or without further processing of the outcome, as at least part of a reply to the request. To that end, a cloud computing, distributed computing, or client-server computing technology may be used, for example.

Although FIG. 3 illustrates one example of the electronic device 301 in the network environment 300, various changes can be made to FIG. 3. For example, various components in FIG. 3 can be combined, further subdivided, or omitted and additional components can be added according to particular needs. As a particular example, the processor 320 can be further divided into additional processors, such as one or more central processing units (CPUs), one or more graphics processing units (GPUs), one or more neural networks, and the like. Also, while FIG. 3 illustrates the electronic device 301 configured as a mobile telephone, tablet, or smartphone, the electronic device 301 can be configured to operate as other types of mobile or stationary devices.

Figure 4B:
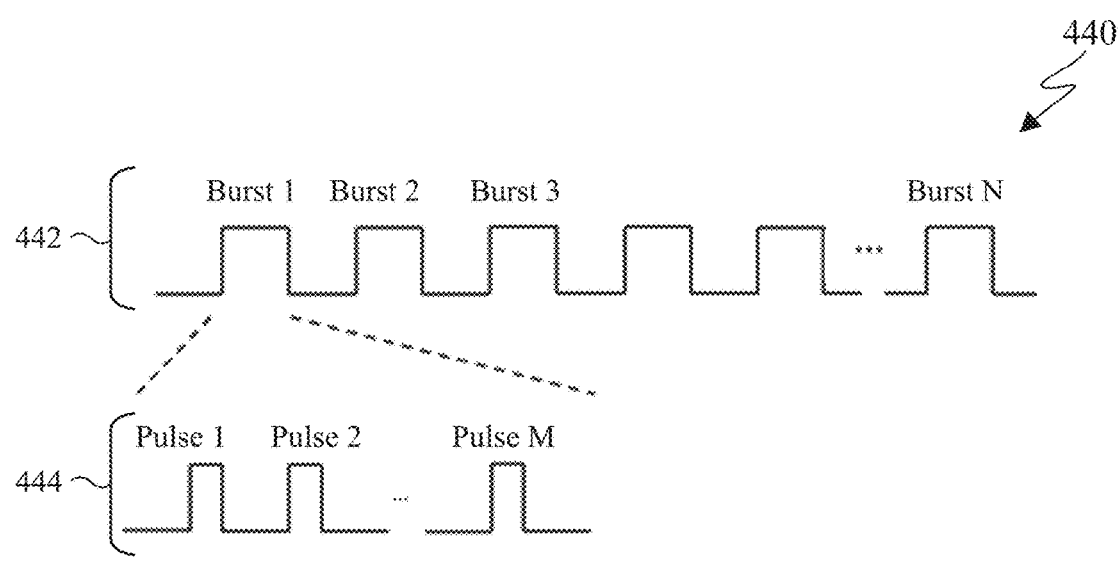
FIG. 4B illustrates an example frame structure according to embodiments of this disclosure.

FIG. 4A illustrates an example architecture of a monostatic radar in accordance with an embodiment of this disclosure. FIG. 4B illustrates an example frame structure 440 in accordance with an embodiment of this disclosure. The embodiments of FIGS. 4A and 4B are for illustration only and other embodiments can be used without departing from the scope of the present disclosure.

FIG. 4A illustrates an electronic device 400 that includes a processor 402, a transmitter 404, and a receiver 406. The electronic device 400 can be similar to any of the client devices 106-114 of FIG. 1, the server 104 of FIG. 1, the electronic device 200 of FIG. 2, or the electronic device 301 of FIG. 3. The processor 402 is similar to the processor 240 of FIG. 2 and the processor 320 of FIG. 3. Additionally, the transmitter 404 and the receiver 406 can be included within the measuring transceiver 270 of FIG. 2.

The transmitter 404 transmits a signal 414 to the target object 408. The target object 408 is located a distance 410 from the electronic device 400. For example, the transmitter 404 transmits a signal 414 via an antenna. In certain embodiments, the target object 408 correspond to an object that forms the environment around the electronic device 400. The signal 414 is reflected off of the target object 408 and received by the receiver 406, via an antenna. The signal 414 represents one or many signals that can be transmitted from the transmitter 404 and reflected off of the target object 408. The processor 402 can identify the information associated with the target object 408, such as the speed the target object 408 is moving and the distance the target object 408 is from the electronic device 400, based on the receiver 406 receiving the multiple reflections of the signals, over a period of time.

Leakage 416 represents radar signals that are transmitted from the antenna associated with transmitter 404 and are directly received by the antenna associated with the receiver 406 without being reflected off of the target object 408.

In order to track the target object 408, the processor 402 analyzes a time difference 412 from when the signal 414 is transmitted by the transmitter 404 and received by the receiver 406. It is noted that the time difference 412 is also referred to as a delay, as it indicates a delay between the transmitter 404 transmitting the signal 414 and the receiver 406 receiving the signal after the signal is reflected or bounced off of the target object 408. Based on the time difference 412, the processor 402 derives the distance 410 between the electronic device 400, and the target object 408. Additionally, based on multiple time differences 412 and changes in the distance 410, the processor 402 derives the speed that the target object 408 is moving.

Monostatic radar is characterized for its delayed echo as the transmitter 404 of the radar signal and the receiver 406 of the radar signal essentially at the same location. In certain embodiments, the transmitter 404 and the receiver 406 are co-located either by using a common antenna or nearly co-located but use separate but adjacent antennas. Monostatic radars are assumed coherent such that the transmitter 404 and the receiver 406 are synchronized via a common time reference.

Pulse radar is generated as a realization of a desired radar waveform, modulated onto a radio carrier frequency, and transmitted through a power amplifier and antenna, such as a parabolic antenna. In certain embodiments, the pulse radar is omnidirectional. In other embodiments, the pulse radar is focused into a particular direction. When the target object 408 is within the field of view of the transmitted signal and within a distance 410 from the radar location, then the target object 408 will be illuminated by RF power density (W/m²), $p_t$, for the duration of the transmission. Equation (1) describes the first order of the power density, $p_t$.

$$p_t = \frac{P_T}{4\pi R^2} G_T = \frac{P_T}{4\pi R^2} \frac{A_T}{(\lambda^2/4\pi)} = P_T \frac{A_T}{\lambda^2 R^2} \quad (1)$$

Referring to Equation (1), $P_T$ is the transmit power (W). $G_T$ describes the transmit antenna gain (dBi) and $A_T$ is an effective aperture area (m²). $\lambda$ corresponds to the wavelength of the radar signal RF carrier signal (m), and R corresponds to the distance 410 between the antenna and the target object 408. In certain embodiments, effects of atmospheric attenuation, multi-path propagation, antenna loss and the like are negligible, and therefore not addressed in Equation (1).

The transmit power density impinging onto the target object 408 surface can cause reflections depending on the material, composition, surface shape and dielectric behavior at the frequency of the radar signal. In certain embodiments, only direct reflections contribute to a detectable receive signal since off-direction scattered signals can be too weak to be received by at the radar receiver. The illuminated areas of the target with normal vectors pointing back at the receiver can act as transmit antenna apertures with directives (gains) in accordance with their effective aperture areas. Equation (2), below, describes the reflective back power.

$$P_{refl} = p_t A_t G_t \sim p_t A_t r_t \frac{A_t}{\lambda^2/4\pi} = p_t RSC \quad (2)$$

In Equation (2), $P_{refl}$ describes the effective isotropic target-reflected power (W). The term, $A_t$, describes the effective target area normal to the radar direction (m²). The term $r_t$ describes the reflectivity of the material and shape, which can range from [0, . . . , 1]. The term $g_t$ describes the corresponding aperture gain (dBi). RSC is the radar cross section (m²) and is an equivalent area that scales proportional to the actual reflecting area-squared inversely proportional with the wavelength-squared and is reduced by various shape factors and the reflectivity of the material itself. Due to the material and shape dependency, it is difficult to deduce the actual physical area of a target from the reflected power, even if the distance 410 to the target object 408 is known.

The target reflected power at the receiver location results from the reflected power density at the reverse distance 410 collected over the receiver antenna aperture area. Equation (3), below, describes the received target reflected power. It is noted that $P_R$ is the received target reflected power (W) and $A_R$ is the receiver antenna effective aperture area (m²). In certain embodiments, $A_R$ is the same as $A_r$.

$$P_R = \frac{P_{ref1}}{4\pi R^2} A_R = P_T \cdot RSC \frac{A_T A_R}{4\pi \lambda^2 R^4} \quad (3)$$

A radar system can be used as long as the receiver signal exhibits sufficient signal-to-noise ratio (SNR). The value of SNR depends on the waveform and detection method. Equation (4), below, describes the SNR. It is noted that kT is the Boltzmann constant multiplied by the current temperature. B is the radar signal bandwidth (Hz). F is the receiver noise factor which is a degradation of the receive signal SNR due to noise contributions of the receiver circuit itself $$SNR = \frac{P_R}{kT \cdot B \cdot F} \quad (4)$$

When the radar signal is a short pulse of duration or width, $T_p$, the delay or time difference 412 between the transmission and reception of the corresponding echo is described in Equation (5). τ corresponds to the delay between the transmission and reception of the corresponding echo and equal to Equation (5). c is the speed of light propagation in the air. When there are multiple targets at different distances, individual echoes can be distinguished only if the delays differ by at least one pulse width. As such, the range resolution of the radar is described in Equation (6). A rectangular pulse of a duration $T_P$ exhibits a power spectral density as described in Equation (7) and includes a first null at its bandwidth as shown in Equation (8). The range resolution of a radar signal is connected with the bandwidth of the radar waveform is expressed in Equation (9).

$\tau = 2R/c$ (5)

$\Delta R = c\Delta\tau/2 = cT_P/2$ (6)

$P(f) \sim (\sin(\pi f T_P)/(\pi f T_P))^2$ (7)

$B = 1/T_P$ (8)

$\Delta R = c/2B$ (9)

Depending on the radar type, various forms of radar signals exist. One example is a Channel Impulse Response (CIR). CIR measures the reflected signals (echoes) from potential targets as a function of distance at the receive antenna module, such as the measuring transceiver 270 of FIG. 2. In certain embodiments, CIR measurements are collected from transmitter and receiver antenna configurations which when combined can produce a multidimensional image of the surrounding environment. The different dimensions can include the azimuth, elevation, range, and Doppler.

The example frame structure 440 of FIG. 4B illustrates an example raw radar measurement based on a pulse compression radar. The frame structure 440 describes that time is divided into frames, where a frame is further divided into bursts 442, and several pulses 444 can be transmitted by the radar transmitter in each burst 442. For example, the example frame structure 440 includes burst 1, burst 2, burst 3, through bust N. Each bust includes multiple pulses 444, such as pulse 1, pulse 2 through pulse M. In certain embodiments, different transmit and receive antenna configurations activate for each pulse or each burst. In certain embodiments, different transmit or receive antenna configurations activate for each pulse or each burst. It is noted that although the example frame structure 440 illustrates only one burst type, multiple burst types can be defined in the same frame, where each burst type includes a different antenna configuration.

In certain embodiments, each pulse or burst may have a different transmit/receive antenna configuration corresponding to the active set of antenna elements and corresponding beamforming weights. For example, each of the M pulses in a burst can have different transmit and receive antenna pair allowing for a spatial scan of the environment (such as using beamforming), and each of the bursts 442 all repeat the same pulses. As such, all of the signals from all the pulses within a burst provide a complete scan of the radar field of view, and the repetitions across the bursts provide a way to capture the temporal variation. For another example, all of the M pulses can use the same antenna configuration to boost the signal strength by averaging the M pulses, and the N bursts may all repeat the same pulses. In both these examples, the burst domain can be referred to as the slow time domain in the radar literature. The burst or slow time domain captures the temporal variation of the radar signals, which can be processed to obtain Doppler (or speed) information.

The example frame structure 440 illustrates uniform spacing between pulses and bursts. In certain embodiments, any the spacing, even non-uniform spacing, between pulses and bursts can be used. In other embodiments, the radar measurement is a three-dimensional complex impulse response (CIR) matrix, where the first dimension can correspond to the burst index, the second dimension can correspond to the pulse index and the third dimension can correspond to the delay tap index. The delay tap can be translated to the measurement of range or equivalently the time of flight of the received signal. For example, a delay tap is based on the time between the transmission and reception of the corresponding echo.

Although FIGS. 4A and 4B illustrate electronic device 400 and radar signals various changes can be made to FIGS. 4A and 4B. For example, different antenna configurations can be activated. FIGS. 4A and 4B do not limit this disclosure to any particular radar system or apparatus.

Figure 5:
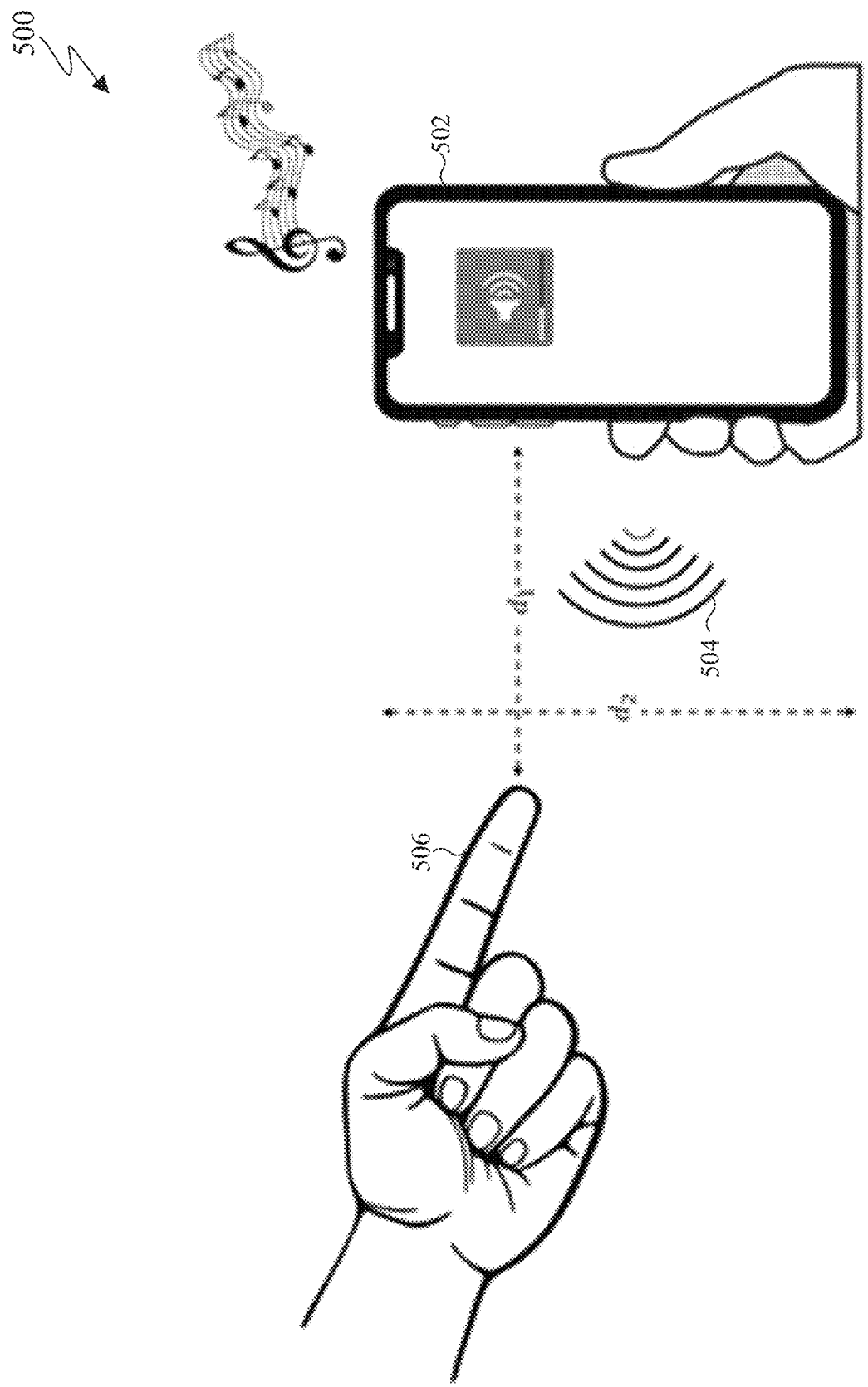
FIG. 5 illustrates an electronic device detecting a gesture according to embodiments of this disclosure

FIG. 5 illustrates an embodiment 500 of an electronic device 502 detecting a gesture according to embodiments of this disclosure. The embodiment 500 is for illustration only. Other embodiments can be used without departing from the scope of the present disclosure.

The electronic device 502 can be configured similar to any one of the client device 106-114 of FIG. 1, the electronic device 400 of FIG. 4A, and can include internal components similar to that of electronic device 200 of FIG. 2 and the electronic device 301 of FIG. 3.

As illustrated in FIG. 5, the electronic device 502 is configured to emit signals 504, such as radar signals towards a finger 506 of a user while the finger is moving (performing a gesture) relative to the electronic device 502. The distance D1 and the distance D2 change as the finger 506 moves while performing a gesture. While only two distances are illustrated in FIG. 5, the electronic device 502 can detect changes in the distances in the X, Y, and Z coordinates. The electronic device 502 receives reflections of the signals 504 that are reflect off of the finger 506 of the user over a period of time. Based on the changes in the distances D1 and D2 (between the finger 506 and the electronic device 502) as the finger 506 moves, the electronic device 502 can identify a gesture that is performed via the finger 506 of the user. After identifying the gesture, electronic device 502 performs an action indicated by the gesture. For example, based on the changes in the distances D1 and D2 over a period of time the electronic device can alter volume that is output through a speaker on the electronic device 502.

Although FIG. 5 illustrates an electronic device 502 and radar signals various changes can be made to FIG. 5. For example, different actions can be performed for a given gesture. FIG. 5 does not limit this disclosure to any particular radar system or apparatus.

Figure 6A:
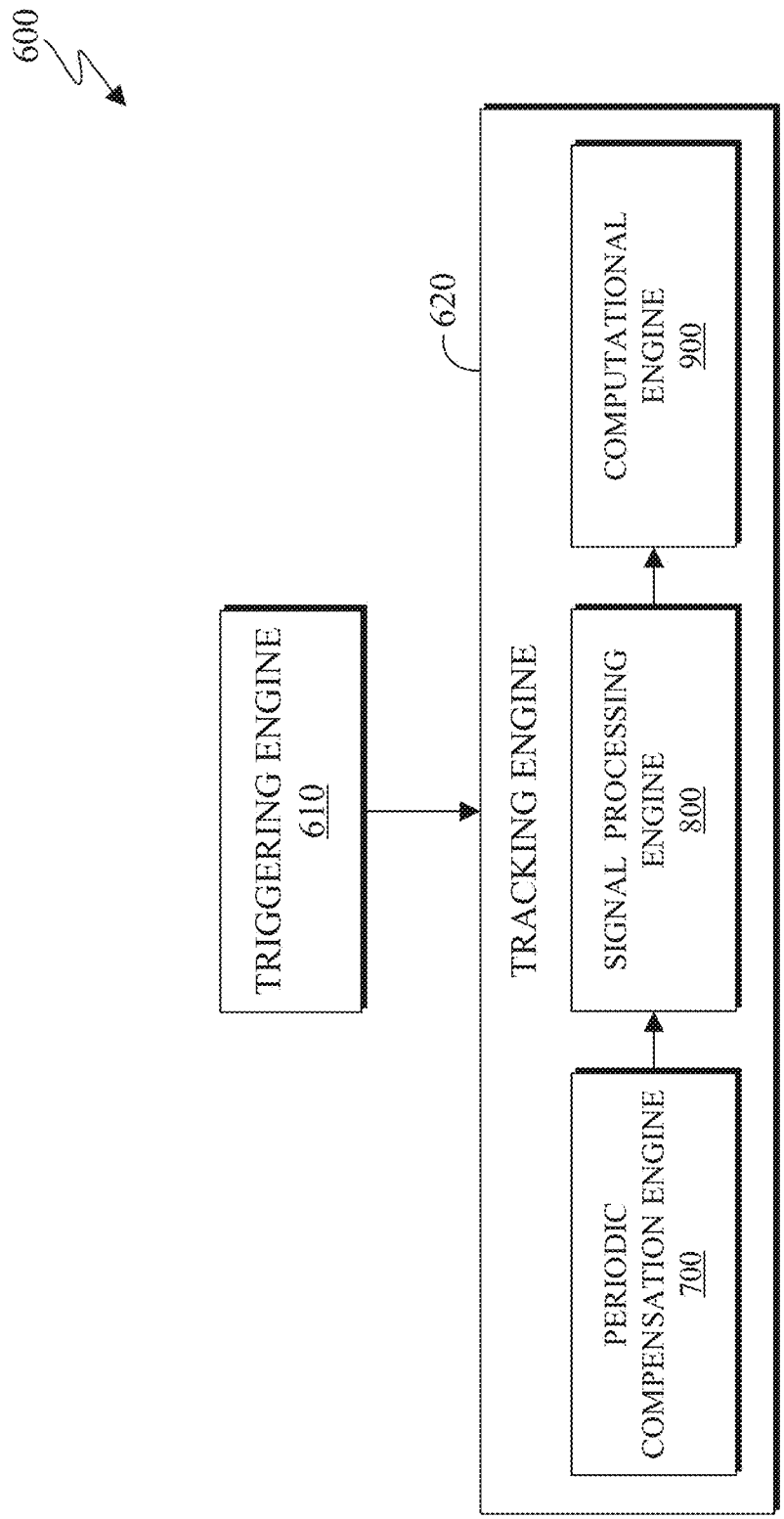
FIG. 6A illustrates a signal processing diagram for gesture recognition according to embodiments of this disclosure.
Figure 6B:
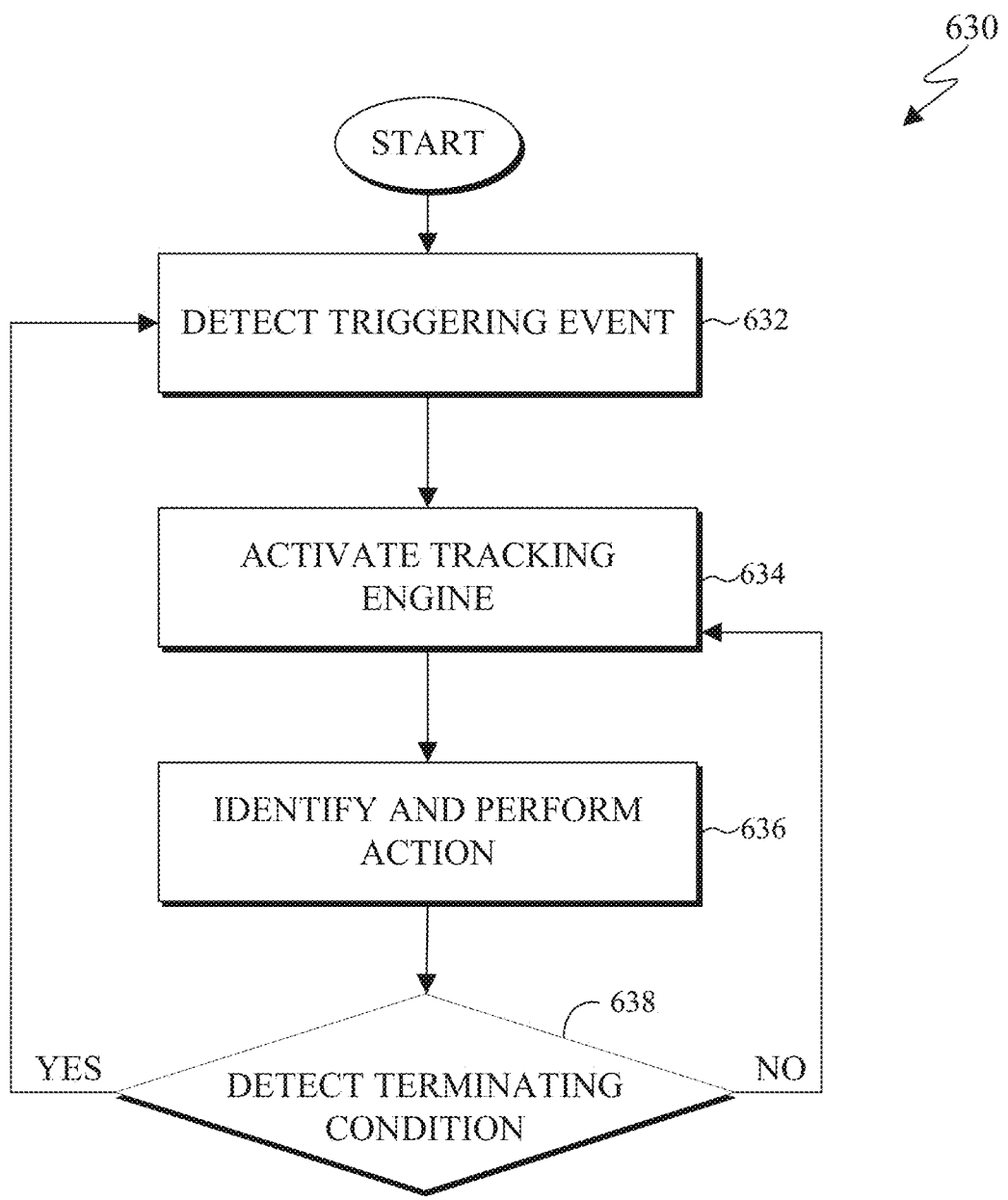
FIG. 6B illustrates a flowchart for gesture recognition according to embodiments of this disclosure.
Figure 6D:
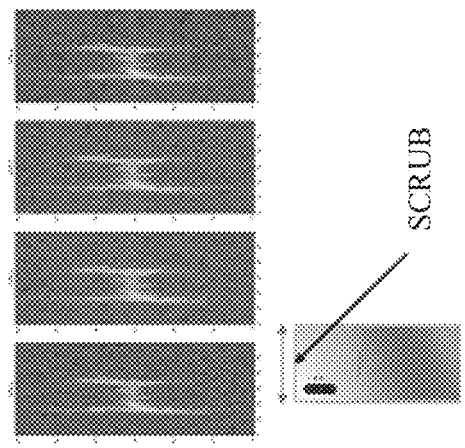
FIGS. 6C, 6D, and 6E illustrate example trigging events with corresponding signals according to embodiments of this disclosure.
Figure 6E:
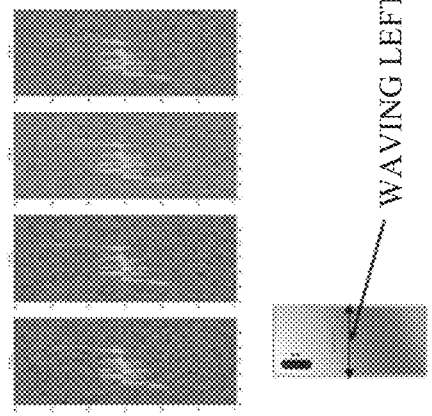
Figure 6C:
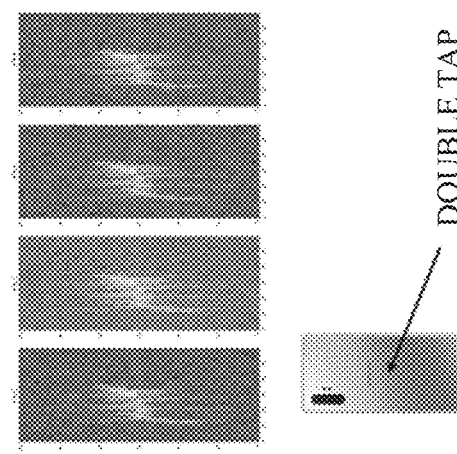

FIG. 6A illustrates a signal processing diagram 600 for gesture recognition according to embodiments of this disclosure. FIG. 6B illustrates a flowchart 630 for gesture recognition according to embodiments of this disclosure. FIGS. 6C-6E illustrates example trigging events with corresponding signals according to embodiments of this disclosure. The embodiments of the signal processing diagram 600, the flowchart 630, and the trigging events with corresponding signals of FIGS. 6C-6E are for illustration only. Other embodiments can be used without departing from the scope of the present disclosure.

Embodiments of the present disclosure provide methods and an apparatus identifying a gesture using a radar sensor, an ultrasonic sensor, or the like in order to perform an action corresponding to the gesture. Since radar data can include a significant amount of irrelevant information, the embodiments of the present disclosure also provide methods for processing the data in order to extract relevant features and refining the features for gesture identification.

As shown in FIG. 6A, the signal processing diagram 600 for gesture recognition can be performed by any one of the client device 106-114 of FIG. 1, the electronic device 400 of FIG. 4A the electronic device 502 of FIG. 5 and can include internal components similar to that of electronic device 200 of FIG. 2 and the electronic device 301 of FIG. 3. However, the signal processing diagram 600 as shown in FIG. 6A could be used with any other suitable electronic device and in any suitable system, such as when performed by the electronic device 200.

The signal processing diagram 600 is generally used to capture and process signals for gesture recognition in order to perform an action corresponding to the gesture. Depending on the implementation, the signal processing diagram 600 can include a radar transceiver that transmits radar signals and receives signals that reflect off of an object, such as the finger of a suer, while performing a gesture. For example, using a mmWave radar signal, the signal processing diagram 600 can track movement of a small objects for gesture recognition. The recognized gestures can be a natural way for a user to interact with an electronic device, such as the electronic device 200 of FIG. 2.

The signal processing diagram 600 includes two components a triggering engine 610 and a tracking engine 620. In certain embodiments, the triggering engine 610 and the tracking engine 620 represent one or more processors such as the processor 240 of FIG. 2. The triggering engine 610 determines when a situation occurs for object tracking and gesture identification via the tracking engine 620.

In certain embodiments, the triggering engine 610 is not included in the signal processing diagram 600. For example, the tracking engine 620 can track motions to determine whether the motion corresponds to a pre-defined gesture and subsequently perform an action corresponding to the identified gesture. For instance, if the tracking engine 620 is associated with a device that detects when a human falls, such as at a senior care facility, the tracking engine 620 will continually monitor the area for motion and upon determining that a detected motion corresponds to a human falling, the device can perform a function, such as notifying the staff of the location that the person fell.

The triggering engine 610 detects and recognizes a particular input, and upon recognizing the particular input, the triggering engine 610 activates the tracking engine 620. The particular input can be based on a detection of a particular button (soft button or physical button) on the electronic device 200 being pressed. The particular input can be based on a detection of a particular tapping or swipe input on the electronic device 200. In certain embodiments, the particular input that activate the tracking engine 620 can be a pre-defined gesture. The predefined gesture can be based on a particular movement that includes a unique radar signature. A signature signal can be based on multiple movements with distinctive patterns that do not easily generate false detections due to random gestures. For example, a signature gesture can include at least one repetition in one or more feature domains such as Doppler, Velocity, range, and the like. It is noted that the reputation of a signature gesture can include a same gesture repeated, a flipped version of the gesture, or a combination thereof. Due to the repetition of the signature gesture, it unlikely that a signature gesture is unintentionally performed by a user. FIGS. 6C-6E describe various gestures and the corresponding signal that is used to identify a signature signal for activating the tracking engine 620.

The triggering engine 610 can prevent the tracking engine 620 from tracking an inadvertent gesture in order to prevent the electronic device 200 from performing an action for an unintentional or a false gesture. For example, when the triggering engine 610 detects an input (such as when a physical or soft button of the electronic device 200 is pressed or when a particular gesture that includes a signature signal is performed), the triggering engine 610 can activate the tracking engine 620. For instance, if the triggering engine 610 detects a double tap on the electronic device 200, a scrubbing motion, a waving motion, or the like, along certain portions of the electronic device 200, them the triggering engine 610 can activate the tracking engine 620.

The tracking engine 620 tracks the object, identifies the gesture, and then performs an action that corresponds to the identified gesture. In certain embodiments, the tracking engine 620 outputs the identified gesture as an input, similar to the input 250 of FIG. 2, such that the electronic device 200 performs an action corresponding to the gesture. Upon identifying a termination condition, such as the gesture stops, or a predetermined time period elapses, the tracking engine 620 is deactivated. The tracking engine 620 can be deactivated until the trigging engine 610 detects and recognizes another particular gesture.

The tracking engine 620 includes a periodic compensation engine 700, a signal processing engine 800 and a computational engine 900. In certain embodiments, the periodic compensation engine 700 is omitted and not included in the signal processing diagram 600. In certain embodiments the tracking engine 620 also includes a normalization engine.

The periodic compensation engine 700 modifies the signal due to hardware imperfections. In certain embodiments, the periodic compensation engine 700 modifies the signal by compensating the signal for periodic variation behavior in the CIR. For example, the periodic compensation engine 700 compensates for periodic variation behavior in the CIR, sch as variations caused by temperature change during the radar transmission frame. A periodic variation is due to the response changes of a device affects the CIR for all delay taps. In certain embodiments, the periodic compensation engine 700 compensates for the variations by using one delay tap to estimate the variation. The estimated variation is referred to a compensation coefficient and can be used to compensate for all other delay taps. The periodic compensation engine 700 compensates for variations in the burst or slow time domain. Therefore, the compensation coefficients are computed for each burst. The periodic compensation engine 700 and how to identify the compensation coefficients are described in greater detail below in FIG. 7.

The signal processing engine 800 processes the raw radar signals (or other type of signals) to remove noise and irrelevant data. For example, the signal processing engine 800 prepares and transforms the data into a form that can be used by the computational engine 900. In certain embodiments, the signal processing engine 800 removes irrelevant information in the radar data. The signal processing engine 800 can also perform an adaptive thresholding to reduce the level of noise. Additionally, the signal processing engine 800 converts the extracted features from a TVD data into a standardized form that is uniformed across various sensor platforms. In certain embodiments, the signal processing engine 800 refines the data to further reduce noise in the standardized form. The signal processing engine 800 is described in greater detail below in FIGS. 8A-8E.

The computational engine 900 receives the streamed processed data from the signal processing engine 800 and detects an underlining pattern in the data to generate tracking information for identifying the gesture. The tracking information corresponds an identity of a gesture. Based on the identified gesture, the electronic device 200 can perform a corresponding action, such as increasing or decreasing the volume of sound that is output through a speaker such as the speaker 230 of FIG. 2, answer an incoming phone call, open or close an application, and the like. In certain embodiments, the computational engine 900 performs a recognition task to identify the gesture using a neural network, such as a convolutional neural network (CNN), a recurrent neural network (RNN), and the like. The computational engine 900 is described in greater detail below in FIGS. 9A-9E.

The tracking engine 620 can include an auto-encoder. An auto-encoder encodes the input data for identifying a gesture. In certain embodiments, the auto-encoder can refine the input by applying an anti-aliasing effect on the input data for removing noise. The output of the auto-encoder can be used by the computational engine 900 to train and classify a particular gesture due to the ability of auto-encoder to reconstructing the data. For example, the auto-encoder can randomly corrupt some of the input values by introducing noise and then try to reconstruct the data. In certain embodiments, the auto-encoder can be used to encode the data for removing redundant information form the input. The auto-encoder is described in greater detail below in FIG. 10.

In certain embodiments, the tracking engine 620 can include a normalizing engine (not shown) positioned between the signal processing engine 800 and the computational engine 900. The normalizing engine normalizes and standardizes the signal data before the computational engine 900 receives the streamed processed data in order to provide consistency of the features across the platforms. In certain embodiments, to normalize the data the normalizing engine uses a min-max normalization and rescale the data between [0,1]. A min-max normalization is described in Equation (17) below. In other embodiments, to normalize the data the normalizing engine uses a grey image. A grey image normalization is described in Equation (18) below. In yet other embodiments, to normalize the data, the normalizing engine uses a z-score normalization. A z-score normalization is described in Equation (19) below.

As shown in FIG. 6B, the flowchart 630 can be performed by any one of the client device 106-114 of FIG. 1, the electronic device 400 of FIG. 4A the electronic device 502 of FIG. 5 and can include internal components similar to that of electronic device 200 of FIG. 2 and the electronic device 301 of FIG. 3. However, the flowchart 630 shown in FIG. 6B could be used with any other suitable electronic device and in any suitable system, such as when performed by the electronic device 200.

In step 632, the electronic device 200 detects a triggering event. The triggering engine 610 of FIG. 6A can detect the triggering event. The triggering event is an event that triggers the gesture recognition process. For example, the triggering event can be a gesture that is performed, an input of a particular button. For another example, the triggering event can be an occurrence of a predefined event such as be an incoming phone call. For yet another example, the triggering event can be an application, such as one of the applications 262 of FIG. 2, being executed or running on the electronic device 200. The triggering event can also be the electronic device 200 connecting to another device, such as a car via BLUETOOTH. The triggering event can include the electronic device 200 determining that it is being moved in a certain predefined manner. For instance, a gyroscopic sensor (such as the sensor 265 of FIG. 2) detects motion and the electronic device 200 determines whether the motion matches a predefined pattern. The triggering engine 610 then determines that the motion corresponds a triggering event when the motion matches a predefined pattern.

After the electronic device 200 detects the triggering event of the step 632, the electronic device 200 activates the tracking engine, such as the tracking engine 620 of FIG. 6A, in step 634. Upon the activation of the tracking engine 620 (step 634), the tracking engine 620 identifies the gesture that being performed and performs a corresponding action in step 636. For example, the electronic device 200 can emit signals (such as radar signals) and receive a portion of the emitted signals that are reflected off of an object over a period of time as the object moves. Based on the receives signals the electronic device 200 identifies the gesture and then performs an action corresponding to the gesture. In certain embodiments, the action is based on both the triggering event and the identified gesture. For example, the same gesture can perform different actions based on the triggering event.

After identifying and performing the action in step 636, the electronic device 200, in step 638, determines whether a terminating condition occurs. The terminating condition can be based on a period of time elapsing. For example, the period of time can be since a gesture is identified. For another example, the period of time can be since the tracking engine 620 is activated in step 636. For instance, a timer can commence from the activation of the tracking engine 620 at step 636 and upon an expiration of a predetermined time, causes the termination condition to occur. For yet another example, the terminating condition can be based on identifying a particular gesture.

When no terminating condition occurred, then the electronic device 200 can continues to detect and identify gestures as well as perform corresponding actions with respect to identified gestures. Alternatively, when a terminating condition occurs, the flowchart 630 concludes. For example, the flowchart 630 waits until a new triggering event is detected by the triggering engine 610 at step 632.

Although FIGS. 6A and 6B illustrates one example for gesture recognition various changes may be made to FIGS. 6A and 6B. For example, while shown as a series of steps, various steps in FIGS. 6A and 6B could overlap, occur in parallel, or occur any number of times.

FIGS. 6C, 6D, and 6E illustrates example trigging events with corresponding signals according to embodiments of this disclosure. For example, FIGS. 6C-6E illustrate various gestures and corresponding signals if the triggering event is based on a particular gesture. The signals are represented as a time velocity diagram to illustrating signal responses from different triggering events. The signals represent a change in velocity of a moving object (such as a finger of a user) over a period of time.

In certain embodiments, the gestures of FIGS. 6C-6E do not touch the device, such that the gesture is performed a distance from the device. In certain embodiments, the gestures, such as the gesture of FIG. 6D actually touches the device. FIG. 6C illustrates a signal that corresponds to a double tap gesture with respect to an electronic device. The double tap gesture does not physical touch of the electronic device. For example, the double tap gesture is a gesture where the one or more fingers of the user alternate moving up and down (towards and away) with respect to the electric device. For instance, if one finger is used, the single finger gesture will alternately move towards and away from the electric device. For another instance, if the entire hand if used, the double tap gesture occurs when the hand of the user alternately moves towards and away from the electric device. For yet another instance, if two fingers are used, the double tap gesture occurs when two fingers alternately move towards and away from the device such as when a first finger is closer to the electronic device, the second finger is further away from the electronic device, and as the first finger moves further away from the electronic device, the second finger moves towards the electronic device.

FIG. 6D illustrates a signal that corresponds to a scrubbing gesture with respect to an electronic device. In certain embodiments, a scrubbing gesture is detected when a user physically touches the electronic device. In certain embodiments, instead of scrubbing, a user can trace a portion of the electronic device without touching the electronic device to generate a similar signal.

FIG. 6E illustrates a signal that corresponds to a waving gesture with respect to an electronic device. The waving gesture does not physical touch the electronic device. For example, the waving gesture is detected when a hand of the user moves in alternating horizontal directions with respect to the electric device.

The location and type of gestures illustrated in FIGS. 6C and 6E are examples only. Other gestures at other locations can be performed to for activating the tracking engine 620. The signals of FIGS. 6C, 6D, and 6E are blurry and unclear since these signals represent signals that are captures before the signal processing via the signal processing engine 800 of FIG. 6A.

The gestures of FIGS. 6C-6E include a repetition, such as a back and forth motion, in order to create a signature signal. For example, a signature signal can be based on a motion that includes at least one repetition in one or more feature domains such as Doppler, Velocity, range, and the like. It is noted that the reputation of a signature signal can include a same gesture repeated, a flipped version of the gesture, or a combination thereof.

The illustrated gestures of FIGS. 6C-6E can be applied to different parts of the electronic device such as the top, bottom, center, left, right, front, and back to create different tracking events for activating the tracking engine 620 of FIG. 6A. For another example gestures that are not shown can be performed applied to different parts of the electronic device to create different tracking events for activating the tracking engine 620 of FIG. 6A.

Although FIGS. 6C-6E illustrates an electronic device and various radar signals, various changes can be made to FIG. 6C-6E. For example, different gestures can be performed, which would correspond to different signals. For another example, the gesture can be performed at different locations of the electronic device. FIGS. 6C-6E does not limit this disclosure to any particular radar system or apparatus.

Figure 7:
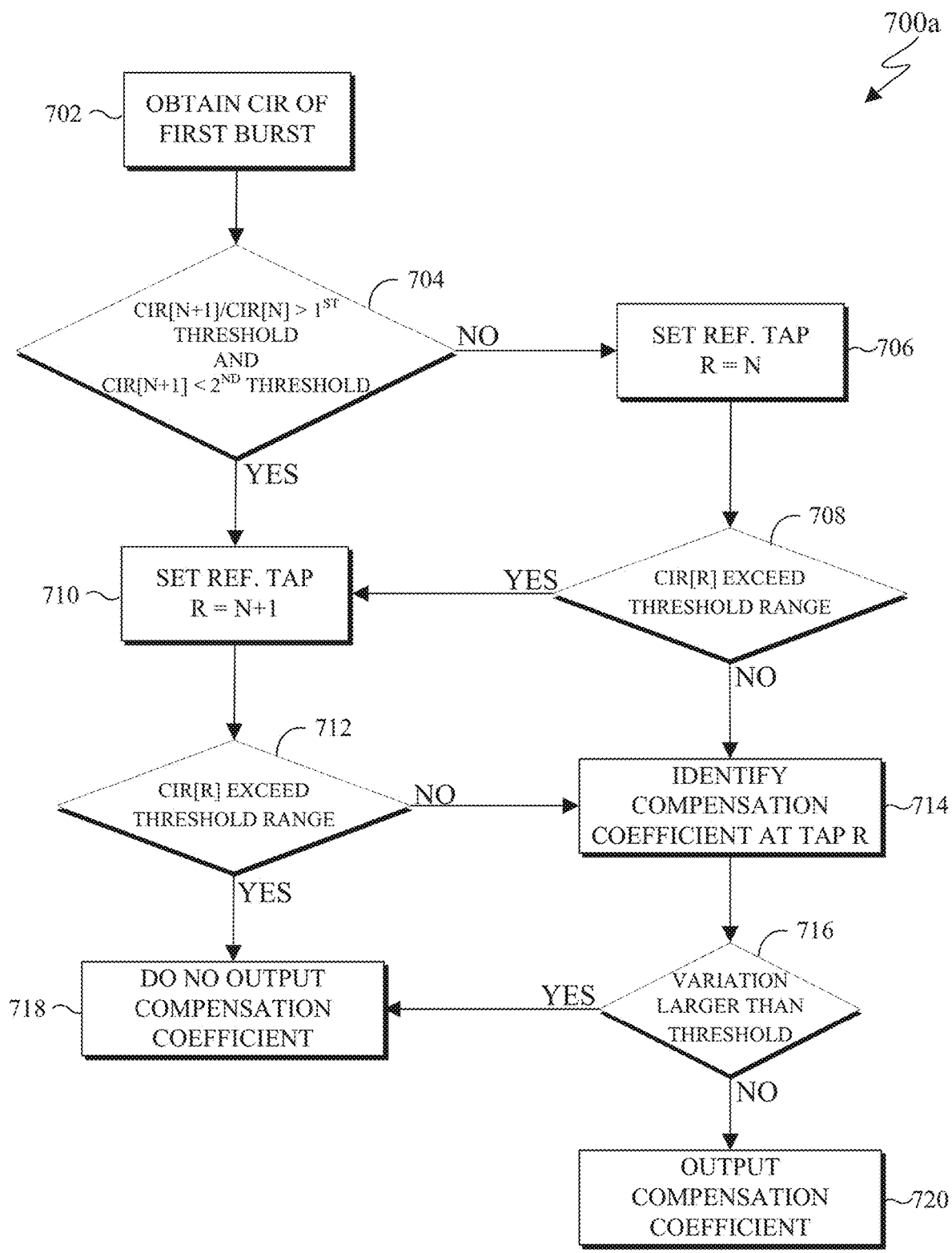
FIG. 7 illustrates a process for compensating a received signal for gesture recognition according to embodiments of this disclosure.

FIG. 7 illustrates a process 700a for compensating a received signal for gesture recognition according to embodiments of this disclosure. The process 700a can be performed by the period compensation engine 700 of FIG. 6A. The embodiment of the process 700a is for illustration only. Other embodiments can be used without departing from the scope of the present disclosure.

As shown in FIG. 7, the process 700a can be performed by any one of the client device 106-114 of FIG. 1, the electronic device 400 of FIG. 4A the electronic device 502 of FIG. 5 and can include internal components similar to that of electronic device 200 of FIG. 2 and the electronic device 301 of FIG. 3. However, the process 700a shown in FIG. 7 could be used with any other suitable electronic device and in any suitable system, such as when performed by the electronic device 200.

The process 700a is generally used to modify a received signal due to hardware imperfections by compensating for periodic variation behaviors in the CIR. As discussed above, the variations can be caused by temperature changes during a signal (such as a radar signal) transmission frame. Since such a periodic variation is due to the response changes of the device, it can affect the CIR for all delay taps. The process 700a provides a method for compensating the periodic variation by using one delay tap to estimate the variations by identifying a compensation coefficient. The compensation coefficient is then used to compensate for all other delay taps.

In certain embodiments, the leakage tap is a good candidate for this task because the leakage, being a direct path between the transmitter and the receiver, tends to be strong and less affected by noise. The leakage tap can be similar to the leakage 416 of FIG. 4A. Embodiments of the present disclosure take into consideration that care must be used to avoid using an incorrect compensation such as when the moving target is too close to the radar and the leakage is affected by that target. A condition of possible incorrect compensation can be detected if the normal periodic variation follows similar patterns for each radar transmission frame, and thus the typical level of variation can be identified based on known from previous measurements. For example, the compensation coefficients over 64 bursts can vary less than 1 dB in amplitude and less than 10 deg. in phase. In this case if the compensation coefficients changes by more than these normal levels of variations, it can be considered abnormal and the compensation is likely not correct. Embodiments of the present disclosure take into consideration that care must be used to avoid saturation cases such as when the signal becomes too strong, and the non-linearity may cause the compensation coefficient to not work properly.

As shown in FIG. 7, a CIR of the first burst is obtained in step 702. In step 704, the CIR of the first burst is checked to compare the amplitude of the leakage tap and its adjacent tap. The purpose is to use the tap with largest signal strength (but not too large that may cause saturation) so that the compensation coefficient estimation is accurate (less affected by noise). The leakage tap index by n. As illustrated, if the CIR amplitude at tap n+1, |CIR[n+1]|, is larger than the leakage tap amplitude, |CIR[n]| by a predefined threshold (such as 3 dB, but other thresholds are possible), and that |CIR[n+1]| is not too large (based on a comparison to another threshold), then the reference tap for computing the compensation coefficient is set to n+1 (step 710). Otherwise, the leakage tap index n is used as the reference tap (step 706).

Next, the CIR amplitude at the reference tap is checked to avoid a case where the CIR is too large or too small (steps 708 and 712). The steps 708 and 712 in order to determine whether there is a saturation in the received signal. If the saturation is too high (larger than an upper threshold), could indicate that the power amplifier might be operating in the non-linear region which would cause the period compensation engine 700 of FIG. 6A and the corresponding process 700a from identifying a compensation value. Similarly, if the SNR is too low (smaller than a lower threshold) could indicate that there is not enough SNR for estimating the compensation. As a result, if the CIR is larger than the upper threshold or lower than the lower threshold, then the corresponding process 700a is unable to from identifying a compensation value from the given CIR.

In step 708, the CIR[r] of tap index n is compared to an upper threshold (denoted as U_th) and a lower threshold (denoted as L_th), creating a condition of (|CIR[r]|>U_th) or (|CIR[r]|<L_th). If CIR[r] is within the range [L_th, U_th] then the decision at step 708 then the process 700a identifies the compensation coefficient at step 714. Alternatively, if CIR[r] is not within the range [L_th, U_th] then the decision at step 708 then the process 700a continues to step 710, where reference tap for computing the compensation coefficient is set to n+1.

After the reference tap for computing the compensation coefficient is set to n+1 (step 710) the process 700a again compares the new CIR to the upper threshold, U_th, and the lower threshold, L_th in step 712. If CIR[r] is not within the range [L_th, U_th] then the decision at step 712 then the process 700a, does not output a compensation coefficient (step 718). Alternatively, if CIR[r] is within the range [L_th, U_th] (of step 712) then the process 700a identifies the compensation coefficient at step 714. Equation (10) describes how compensation coefficients, in step 714, for the b-th burst are identified.

$$\alpha_b = \frac{CIR_1[r]}{CIR_b[r]} \text{ for all } b = 1, 2, \ldots, N \qquad (10)$$

In Equation (10), the number of bursts is N, and $CIR_b[r]$ is the CIR of the b-th burst at the reference tap r. The first burst is used as the anchor. It is noted that any other position can be used as an anchor such as middle burst at index $\lfloor N/2 \rfloor$.

After identifying the compensation coefficient of tap R, the electronic device 200 verifies the range of variation across all the bursts. In step 716, the variation is compared to a threshold. If the variation does not exceed the threshold, the compensation will be applied, and the compensated CIR will be output (step 720). Alternately, if the variation exceeds the threshold, indicates that the compensation will not correct the input. Therefore when the variation exceeds the threshold, then in step 718 the compensation coefficient is not applied, and the original CIR is processed by the signal processing engine 800 of FIG. 6 without compensation.

In order to compensate using the identified compensation coefficient will depend on the device and its usage scenarios. Under a first scenario, such as a normal operation, the leakage tap can be expected to be negligibly affected by the user operation. One such example is when the device equipped with the radar is designed such that in typical use, the user is expected to provide input in an area that does not fall into close proximity to the leakage tap. In this case, the compensation coefficients can be computed on the fly in a real-time manner. For each radar frame, the process 700a is performed by the electronic device 200 for identifying the compensation coefficients $\alpha_b$, and then applied to the range of taps of interest, such as where the object to be tracked is expected to be located. Equation (11), describes applying the compensation coefficients to the CIR at tap n.

$$CIR_{comp,b}[m] = \alpha_b CIR_b[m] \qquad (11)$$

In Equation (11) $CIR_{comp,b}[m]$ denote the compensated CIR of the b-th burst at tap m. That is, Equation (11) describes multiplying the identified compensation coefficients $\alpha_b$, with the compensation coefficients $\alpha_b$, the CIR at tap n.

In another scenario, the desired object to be tracked could be very close to or overlap with the leakage tap under normal operations. In such a case, the on the fly approach cannot be used as the estimation of the compensation coefficients is likely unsuccessful due to the influence of the target at the leakage tap. Therefore, the periodic compensation engine 700 identifies the compensation coefficients whenever possible and store them for later use. In certain embodiments, the periodic compensation engine 700 identifies the compensation coefficient on a regular basis (either periodically or randomly). For example, the process 700a of FIG. 7 can determine whether the computed compensation is valid or not based on past behavior. When the compensation coefficients are determined to be valid the compensation coefficients are saved. For example, the latest compensation coefficients is used. In this case, when a new estimation attempt is successful, the newly obtained compensation coefficients are saved and the old ones in the memory storage are discarded. For another example, newly obtained compensation coefficients could be averaged with other compensation coefficients. The compensation coefficients could be averaged based on weighted average where the freshness of the estimates (i.e., the length of time since they were estimated) could be used to determine the weights, or averaging over the last K estimates, any sort of moving average, or the like. It is noted that when sing the latest available estimates of the compensation coefficients or the averaged compensation coefficients, the compensation coefficients are still applied in a similar manner as described above in Equation (11).

Although FIG. 7 illustrates one example for gesture recognition various changes may be made to FIG. 7. For example, while shown as a series of steps, various steps in FIG. 7 could overlap, occur in parallel, or occur any number of times.

Figure 8A:
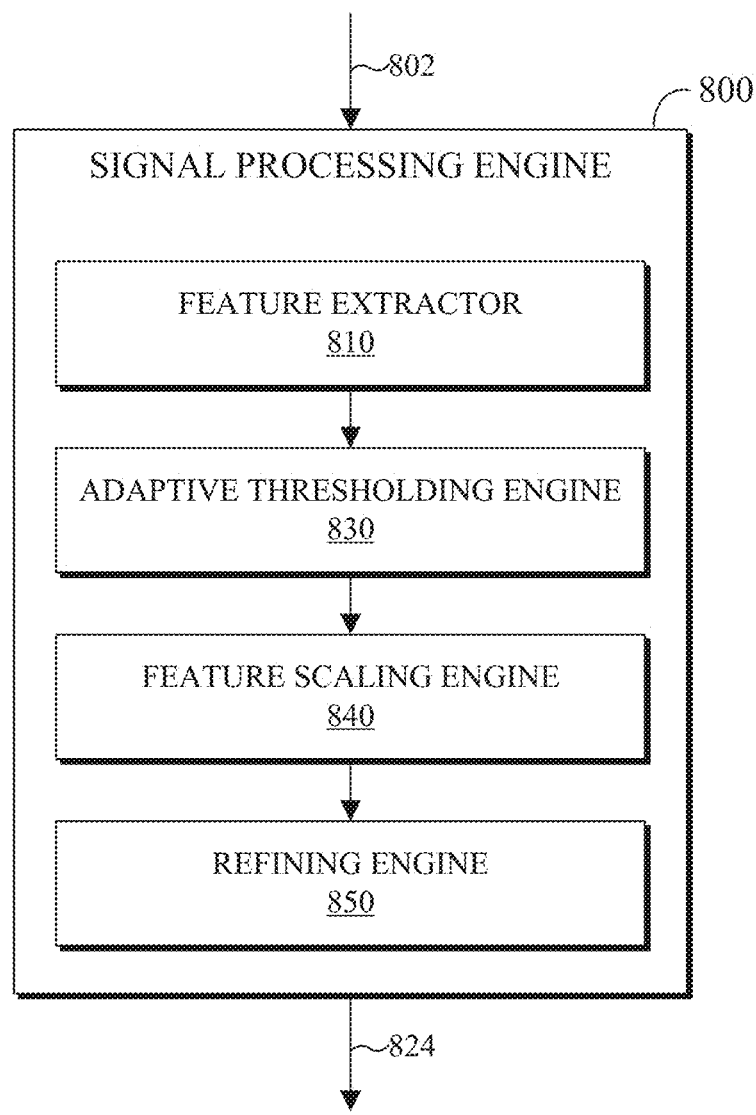
FIG. 8A illustrates a signal processing diagram for gesture recognition according to embodiments of this disclosure.
Figure 8B:
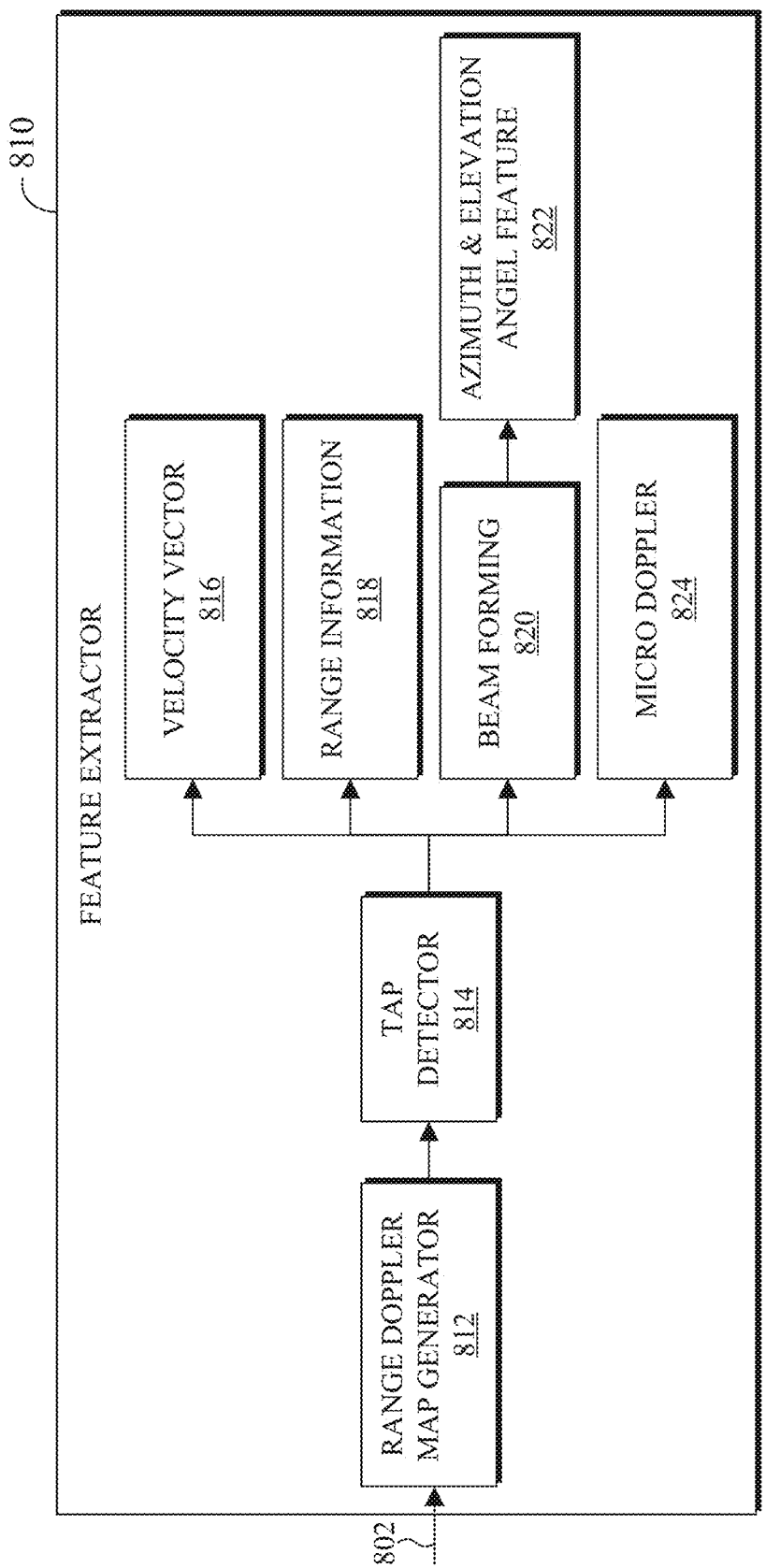
FIG. 8B illustrates extracted features from signal for gesture recognition according to embodiments of this disclosure.
Figure 8C:
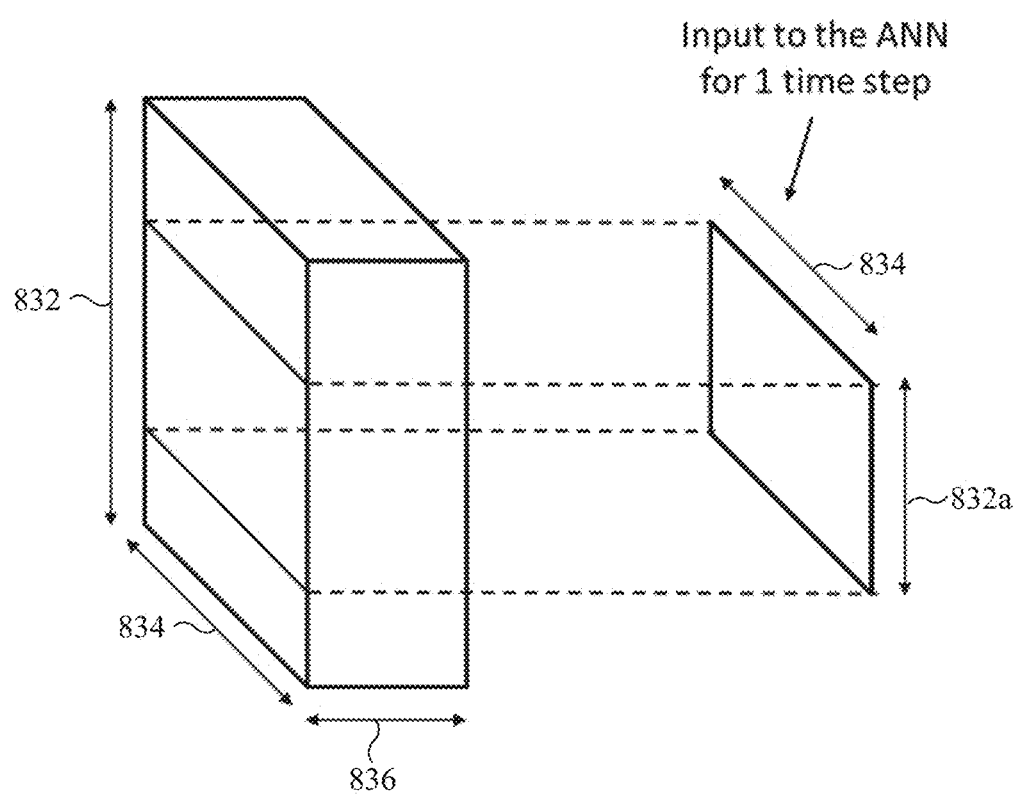
FIG. 8C illustrates a diagram for generating the range doppler map of FIG. 8B according to embodiments of this disclosure.
Figure 8D:
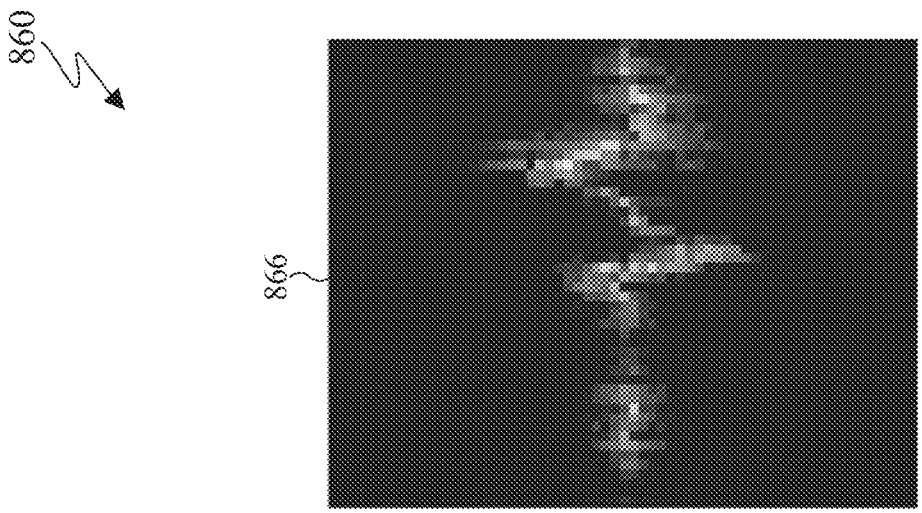
FIG. 8D illustrates an example signal at different stages during the signal processing of FIG. 8A according to embodiments of this disclosure.
Figure 8D:
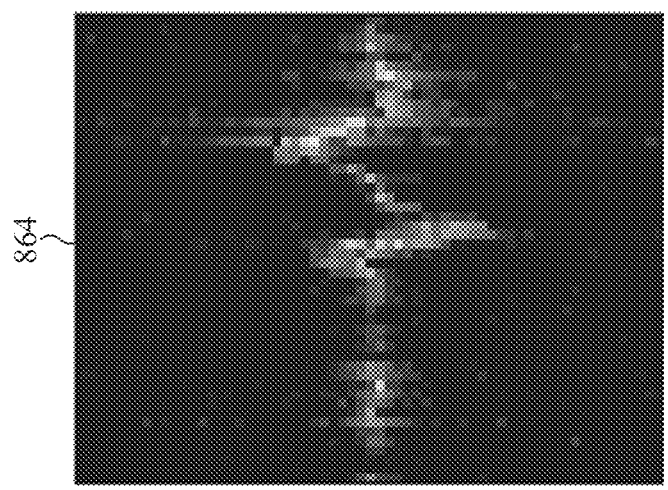
Figure 8D:
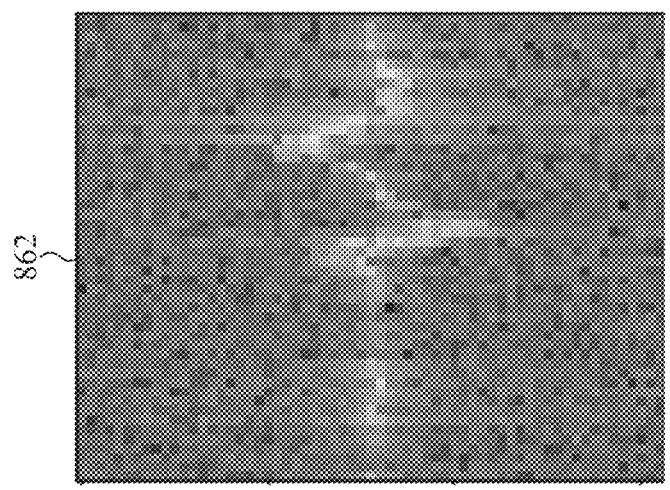

FIG. 8A illustrates a signal processing engine 800 of FIG. 6A for gesture recognition according to embodiments of this disclosure. FIG. 8B illustrates extracting features from signal for gesture recognition using the feature extractor of FIG. 8A according to embodiments of this disclosure. FIG. 8C illustrates a diagram for generating the range doppler map of FIG. 8B according to embodiments of this disclosure. FIG. 8D illustrates an example signal at different stages during the signal processing of FIG. 8A according to embodiments of this disclosure. The embodiments of FIGS. 8A-8D are for illustration only. Other embodiments can be used without departing from the scope of the present disclosure.

As shown in the signal processing engine 800 of FIG. 8A, the feature extractor 810 of FIG. 8B, and the Range Doppler Map (RDM) 830a of FIG. 8C can be performed by any one of the client device 106-114 of FIG. 1, the electronic device 400 of FIG. 4A the electronic device 502 of FIG. 5 and can include internal components similar to that of electronic device 200 of FIG. 2 and the electronic device 301 of FIG. 3. However signal processing engine 800 shown in FIG. 8A and its components (such as the feature extractor 810 of FIG. 8B, and the RDM 830a of FIG. 8C) could be used with any other suitable electronic device and in any suitable system, such as when performed by the electronic device 200.

As shown in FIG. 8A, the signal processing engine 800 receives a signal 802. The signal 802 could be raw signals, such as raw radar signals. The signal 802 can be a CIR. In certain embodiments, the signal 802 is receives from the periodic compensation engine 700 of FIG. 6A. In other embodiments, the signal represents raw data that is receives from a sensor, such as a radar transceiver.

The feature extractor 810 extracts features from the signal 802 for classifying the gesture. In gesture recognition, the features include one or more of range feature, velocity/Doppler feature, RDM feature, TVD, angle feature, and micro Doppler feature of a moving human body part. These features are useful to track the motion of an object, such as a finger, hand, or other body part of a user for identifying the gesture that is being performed. In certain embodiments, only one or some of the features may be needed to identify a particular gesture. The range feature refers to the proximity information between the radar antennas and the gesture object and can be extracted using any radar ranging process. FIG. 8B below describes the feature extraction in greater detail.

In a CIR signal, the delay taps can be translated into range feature. The velocity feature refers to the radial velocity information between the radar antennas and the gesture object and can be obtained using a slow-time processing. Features such as RDM, TVD and micro Doppler can be calculated from range and velocity features. The angle feature refers to the azimuth/elevation angles information of the gesture object relative to the radar antennas and can be extracted with methods such as beamforming.

The adaptive thresholding engine 830 receives the extracted features from the feature extractor 810. When the feature extractor 810 provides the TVD feature, the adaptive thresholding engine 830 performs normalizing and denoising the TVD. The adaptive thresholding engine 830 can also perform normalizing and denoising to other features that are received from the feature extractor 810.

The adaptive thresholding engine 830 identifies an upper bound threshold and a lower bound threshold from the TVD. Using these bounds as a threshold window, the adaptive thresholding engine 830 clips the TVD has the benefit of narrowing down the region of interest in the TVD and effectively removing the noise in the TVD.

In certain embodiments, the adaptive thresholding engine 830 flattens the TVD into a one dimensional array and then sorts the array in ascending order. Equation (12) describes the process of flattening the TVD and sorting the flattened TVD. Equation (13) describes the results of the sorted one dimensional array with n elements.

$$\begin{bmatrix} -51.2 & \cdots & -51.2 \\ \vdots & \ddots & \vdots \\ -51.2 & \cdots & -51.2 \end{bmatrix} \xrightarrow{flatten} [-51.2 \ldots -51.2] \xrightarrow{sorted} \quad (12)$$

$$[-51.23 \ldots 15.2 \; 16.8 \; 17.3]$$

$$x = (x_0, x_1, \ldots, x_{n-1}) \quad (13)$$

After the TVD is flattened and sorted, the adaptive thresholding engine 830 identifies the lower bound and upper bound. The lower bound and upper bound represent a window that can capture the most important portion of the TVD. The lower bound is identified based on the information about the region of interest within the TVD. The smaller the region of interest is, the higher the lower bound is (smaller the window is) and vice versa. Equation (14) describes how the lower bound a is identified.

$$a = x[(n-1) - \lceil n*\alpha \rceil] \quad (14)$$

In Equation (14) n is the length of the TVD array x and $\alpha \in [0,1]$ is the hyper parameter that defines the percentage of the region of interest inside the TVD.

The upper bound, b, can be set to be the last element. For example, the upper bound b, is set to the last element as shown in Equation (15), below $$b = x[n-1] \quad (15)$$

In certain embodiments, there can be abnormal values, such as values that are higher or lower than others. Therefore, embodiments of the present disclosure adjust the position of the window. To do this the differences of two adjacent values on the right most inside the window are checked to ensure that they are not significantly higher than the other. For example, a loop can be used to iterate backward from the current index of the upper bound $i_b$ to move the window to the left (replacing the bounds, $i_a$ and $i_b$) if the condition $\|x[i]-[i-1]\| > \varepsilon$ is not met. Where $\varepsilon$ is a hyper parameter that is empirically determined by examine the training dataset and $i_a$, $i_b$ are the current indices of the lower bound and upper bound relative to x. The goal of this step is to remove some abnormal high noisy value in the TVD that can create misleading signal and distort the TVD input. In certain embodiments, $\varepsilon$ can be calculated by using the average gap between each value in the flattened TVD such as Equation (16) below.

$$\varepsilon = \frac{\sum_{i=1}^{n} x_i - x_{i-1}}{n-1} \quad (16)$$

In certain embodiments, the adaptive thresholding engine 830 performs syntax (1), below to identifies an upper bound threshold and a lower bound from the TVD. As shown in Syntax (1), the input is a flattened and sorted TVD and the output is the upper and lower bounds.

Input: TVD x=flatten(TVD)

x=sort(x)

a_index=len(x)−1−ceil(len(x)*alpha)

b_index=len(x)−1

While abs(x[i]−x[i−1])>epsilon b_index=b_index−1 a_index=a_index−1 a=x[a_index]

$$a=x[b\_index] \tag{1}$$

Output: a,b

In certain embodiments, the adaptive thresholding engine 830 performs an adaptive thresholding on the extracted features of a tracked input by identifying maximum and minimum bounds based on a flattened extracted feature array to produce a clipped feature array. Thereafter the adaptive thresholding engine 830 determines a bound adjustment by comparing whether differences in adjacent values or the average gap between each value of the extracted features exceed a threshold.

The feature scaling engine 840 coverts the clipped TVD (the output of the adaptive thresholding engine 830) to a normalized form in order to generate consistency between the features across the flatforms and the inputs. Using consistent inputs enables the computational engine 900 to reliably identify the gesture. The feature scaling engine 840 rescales the data using different approaches. For example, the feature scaling engine 840 can use a min-max normalization, a grey image, a z-score normalization, and the like.

Equation (17), as shown below, describes the feature scaling engine 840 using a min-max normalization to normalize the clipped TVD. When the feature scaling engine 840 rescales the data using a min-max normalization, the data is recalled between [0,1]. As shown in Equation (17) x is the clipped TVD, the new scaled sample is x'.

$$x' = \frac{x - \min(x)}{\max(x) - \min(x)} \tag{17}$$

Equation (18), as shown below, describes the feature scaling engine 840 rescaling the data to a grey image.

$$x' = \frac{255 * (x - \min(x))}{\max(x) - \min(x)} \tag{18}$$

Equation (19), as shown below, describes the feature scaling engine 840 performing a z-score normalization. As shown in Equation (19), mean $\bar{x}$ and standard deviation $\sigma$ can be computed and then used to standardize each sample.

$$x = \frac{x - \bar{x}}{\sigma} \tag{19}$$

The refining engine 850 refining the input data produced from the feature scaling engine 840 to generate the processed signals 852. In certain embodiments, the refining engine 850 is not included in the signal processing engine 800 such that the feature scaling engine 840 generates the processed signals 852.

In certain embodiments, the refining engine 850 applies a low pass filter to blur the output of the feature scaling engine 840. Blurring the output of the feature scaling engine 840 can reduce noise and refine the signal for further processing by the computation engine 900 of FIG. 6A. In certain embodiments, the refining engine 850 uses a Non-Local Means Denoising process for removing noise from the feature scaling engine 840.

FIG. 8B illustrates the example feature extractor 810 of FIG. 8A according to an embodiment of this disclosure. As illustrated by the feature extractor 810, the signals 802 are converted to RDM by the RDM generator 812. That is, the feature extractor 810 generates the RDM from the signals 802 using an RDM generator 812. It is noted that the signals 802 can be modified by the periodic compensation engine 700 is included in the tracking engine 620 of FIGURE or obtained from the transceiver when the periodic compensation engine 700 is not included in the tracking engine 620. The process of generating the RDM by the RDM generator 812 is described in greater detail in FIG. 8C, below.

Thereafter, the tap detector 814 identifies the region of interest in the RDM. The tap detector 814 selects the taps in the RDM. As such, the selected tap(s) correspond to the moving object. In certain embodiments, the tap detector 814 selects the tap(s) with the largest (or maximum) power in the in RDM.

After identifying the moving tap(s), the features can be calculated for each selected tap. That is, based on the selected tap(s) the feature extractor 810 identifies the selected features. For example, the Doppler/velocity information is obtained based on the velocity vector 816, from RDM, for each corresponding tap. The velocity vector 816 across time (multiple frames) can form the TVD. The range information 818 can be based directly from the index of the detected taps. Beamforming 820 generates the Azimuth and Elevation angle feature 822 since the M pulses are corresponding to M TX-RX antennas pairs. It is noted that the Azimuth and Elevation information may include a significant amount of data, as such, an alternative method to finding the maximal power in beamforming 820 uses the corresponding Azimuth vector for Azimuth angle information and the corresponding Elevation vector for Elevation information. The micro Doppler feature 824 is obtained from the selected tap(s) based on the history of the RDM. The various features and information generated by the feature extractor 810 is outputted to the adaptive thresholding engine 830 of FIG. 8B. It is noted that not all the features (velocity vector 816, range information 818, azimuth and elevation angle feature 822, and micro Doppler 824) are needed.

In certain embodiments, the feature extractor 810 can omit finding various features. For example, the feature extractor 810 can identify the velocity vector 816 feature (while not identifying the range information 818, azimuth and elevation angle feature 822, and the micro Doppler 824) as the input feature to the adaptive thresholding engine 830. For another example, the feature extractor 810 can identify the velocity vector 816 feature and the azimuth and elevation angle feature 822 (which is generated by the beamforming 820) as input features to the adaptive thresholding engine 830, while not identifying the range information 818 and the micro Doppler 824.

FIG. 8C describes how the RDM generator 812 of FIG. 8B generates an RDM. As described above, an RDM is a two-dimensional representation of the radar measurements, where one axis represents distance (or range), and the other axis represents speed (or Doppler). The example RDM 830a, as shown in FIG. 8C, illustrates the preprocessed data being converted into the two-dimensional representation of the radar measurements. The data is three dimensional and based on a burst measurement 832, a tap measurement 834, and an antenna measurement 836 (or channel measurement). The burst measurement 832 is the number of radar bursts. The taps measurement 834 is the number of taps corresponding to range information. The antenna measurement 836 is the number of antennas that are used to broadcast the radar.

Each data frame CIR signal corresponds to a single time step with a complex value tensor. A tensor is a multi-dimensional array. As such a CIR signal can be represented as [b× a× r× t], where b is the number of bursts (corresponding to the burst measurement 832), a is the number antennas (corresponding to the antenna measurement 836), r is the number of repetitions, and t is the number of taps (corresponding to the taps measurement 834). The following example The following example describes how the RDM generator 812 of FIG. 8B generates the RDM representing a two-dimensional representation of the radar measurements. In in the following example, a CIR frame that is represented as [b× a× r× t], is provided with actual values. These value are examples and not intended to be limiting and any other values could be used. In this example, the number of bursts, b, is 64, the number of antennas (or channels), a, is 4, the number of reptations, r, is 4, and the number of taps, t, is 5, which is represented as [64×4×4×5].

First, the RDM generator 812 removes the zero Doppler value. Since most of the background reflections have low Doppler value, one simple way to get rid of all these background signals is to null out low Doppler bins in the range Doppler map. The shape of the data frame is now [(b−1)×a×t], or [63×4×5], using the example values.

Second, the RDM generator 812 performs a Fourier transform (such as a Fast Fourier Transform) along the slow time domain (burst dimension) of the radar signal. Next, the RDM generator 812 averages the data frame over the repetition dimension. Averaging over the repetition dimension boosts the signal strength as well as down samples the data to reduce the complexity. The data frame also switches the tap and channel dimensions. As such, the data frame is now [(b−1)×t×a], or [63×5×4], using the example values.

Fourth, the RDM generator 812 identifies the power level of the signal by identifying the magnitude of the data frame. Additionally due to the small value in the linear scale, which could cause difficulty for the computational engine 900 of FIG. 6A to identify the gesture, the data frame is converted into the decibel scale. For example, the RDM generator 812 applies a $\log_{10}(x)$ to the data in order to convert the data frame into the decibel scale.

Next, the RDM generator 812 removes the two taps in the tap dimension. In certain embodiments, the last two taps are removes. In other embodiments, the first tap and the last tap in the tap dimension are removed. The data frame is now [(b−1)×(t−2)×a], or [63×3×4], using the example values.

Next a certain area of the middle region of the data frame along the burst dimension 832a is extracted by the RDM generator 812. The middle region is extracted since the area above and below the burst dimension 832a is redundant and may not include any activity or useful information. The non-extracted portions (the portion above and the portion below the extracted portion) are discarded. Continuing the example, if the number of bursts is 64, the middle region could be 20 and denoted as d. The data frame is now [20×3×4], using the example values. Finally, the RDM generator 812 averages the antenna dimension to produce a gray scale 2D image. The shape of the data frame is now [d×t] or [20×3].

FIG. 8D illustrates an example signal at different stages during the signal processing of FIG. 8A according to embodiments of this disclosure. The graph 862 illustrates a signal of representing a gesture. For example, the graph 862 can correspond to a raw signal such as the signal 802 of FIG. 8A. The graph 864 illustrates a signal that is output from the adaptive thresholding engine 830. That is, the graph 864 is a clipped TDV. The graph 866 illustrates a signal that is output of the output of the refining engine 850 of FIG. 8A. that ism, the graph 866 is a denoised signal. The graph 866 can correspond to the signal 852 of FIG. 8A. The graphs 862, 864, and 866 plot the speed (Doppler) on the Y axis and time index on the X axis. In certain embodiments, the Y axis can be range or angle instead of Doppler.

Although FIGS. 8A-8E illustrates one example for processing a signal for gesture recognition various changes may be made to FIGS. 8A-8E. For example, while FIGS. 8A and 8B are shown as a series of steps, various steps in FIGS. 8A and 8B could overlap, occur in parallel, or occur any number of times.

Figure 9A:
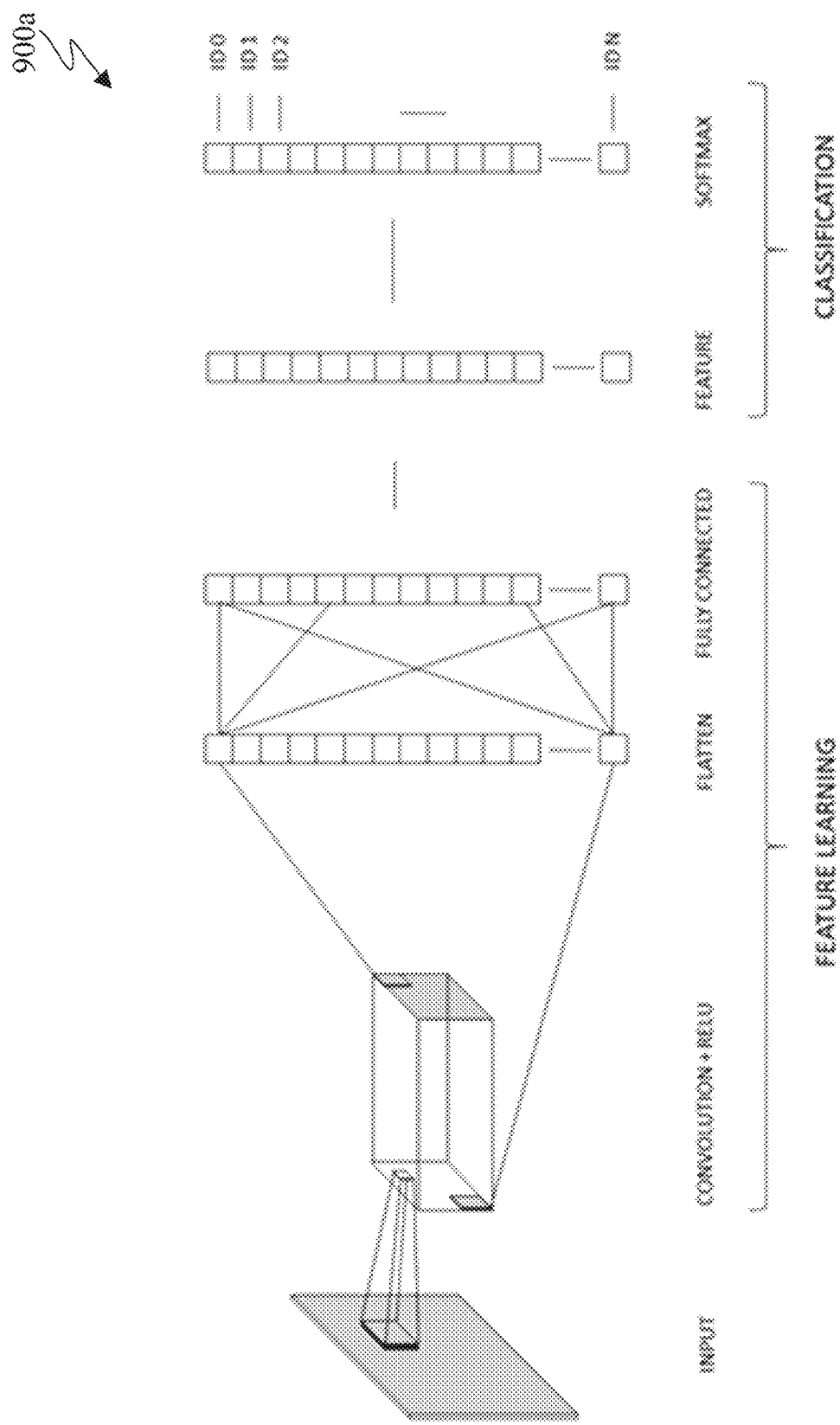
FIG. 9A illustrates an embodiment of an example computational engine in accordance with an embodiment of this disclosure.
Figure 9B:
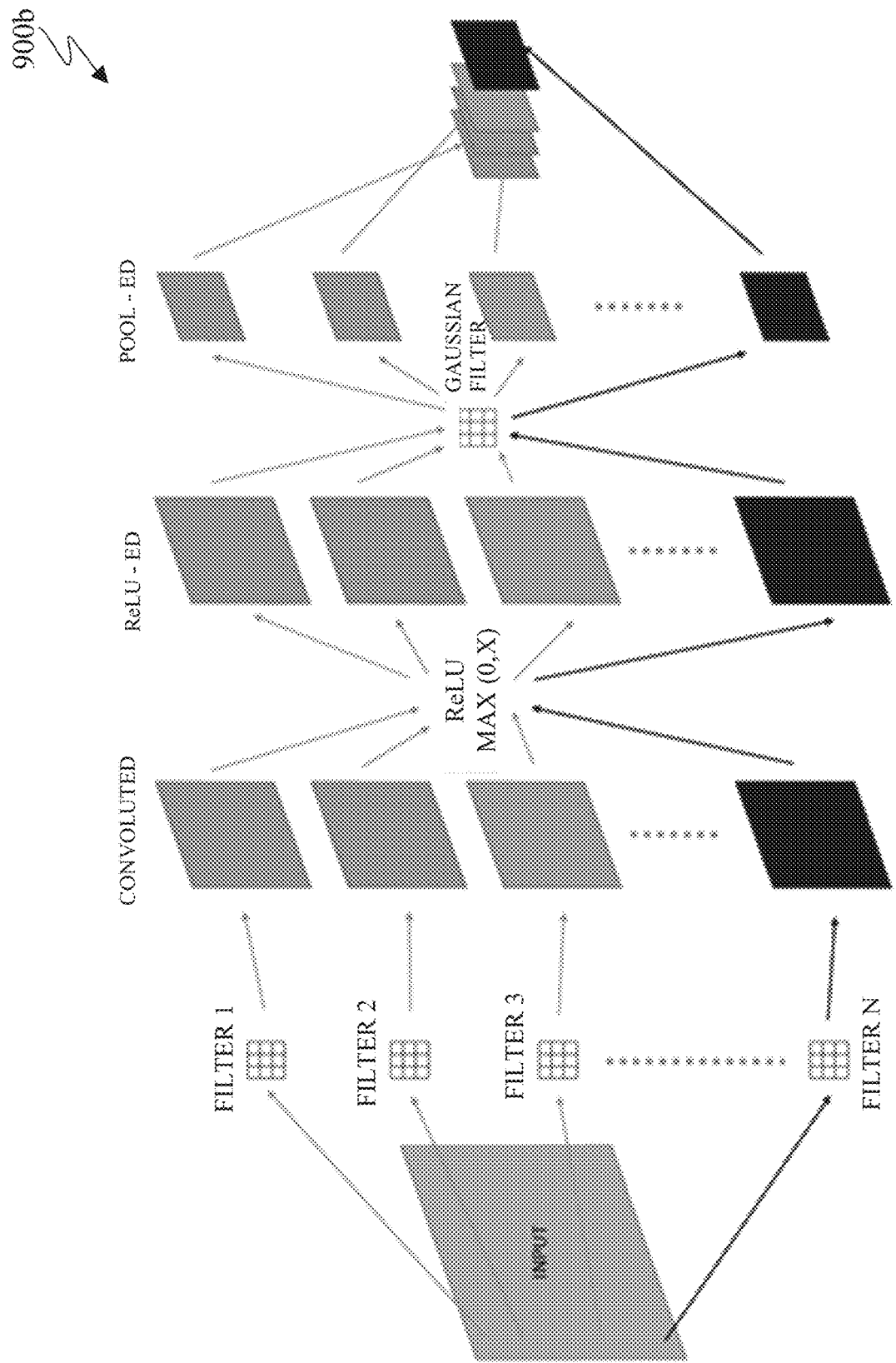
FIG. 9B illustrates an embodiment of an example computational engine with a pooling layer in accordance with an embodiment of this disclosure.
Figure 9C:
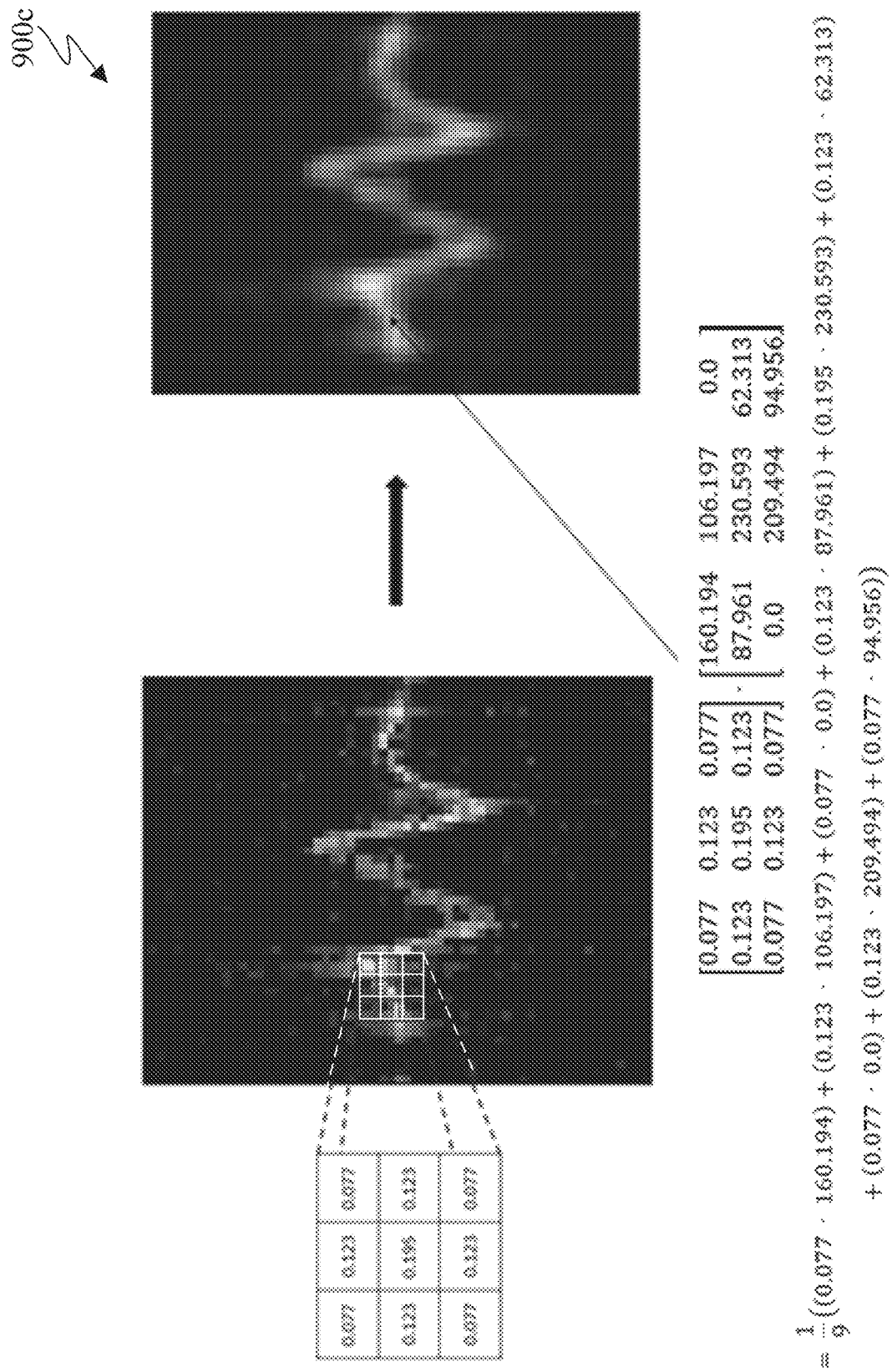
FIG. 9C illustrates an embodiment of example application of the pooling layer of FIG. 9B in accordance with an embodiment of this disclosure.
Figure 9D:
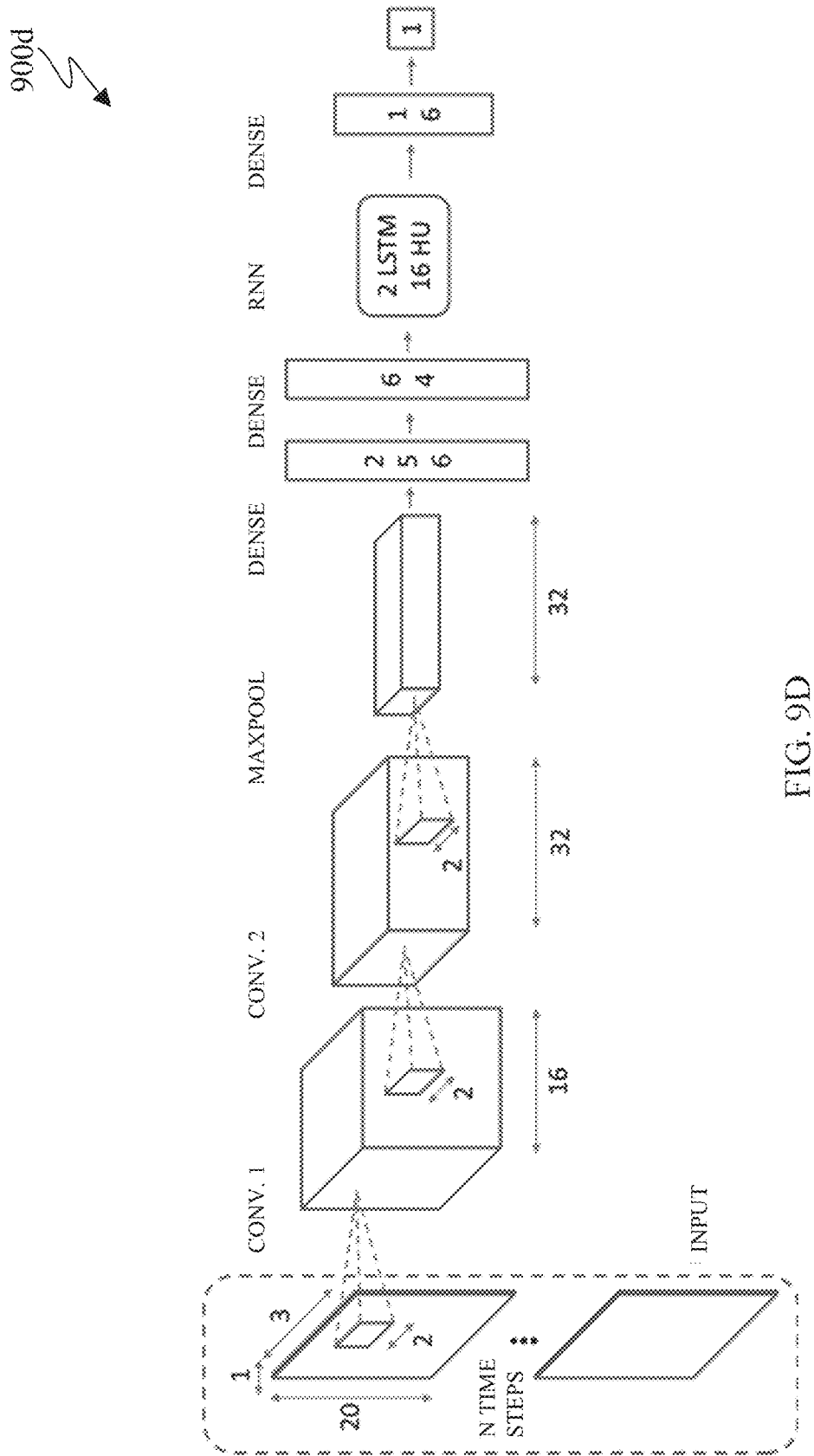
FIGS. 9D and 9E illustrate embodiments of example computational engines in accordance with an embodiment of this disclosure.
Figure 9E:
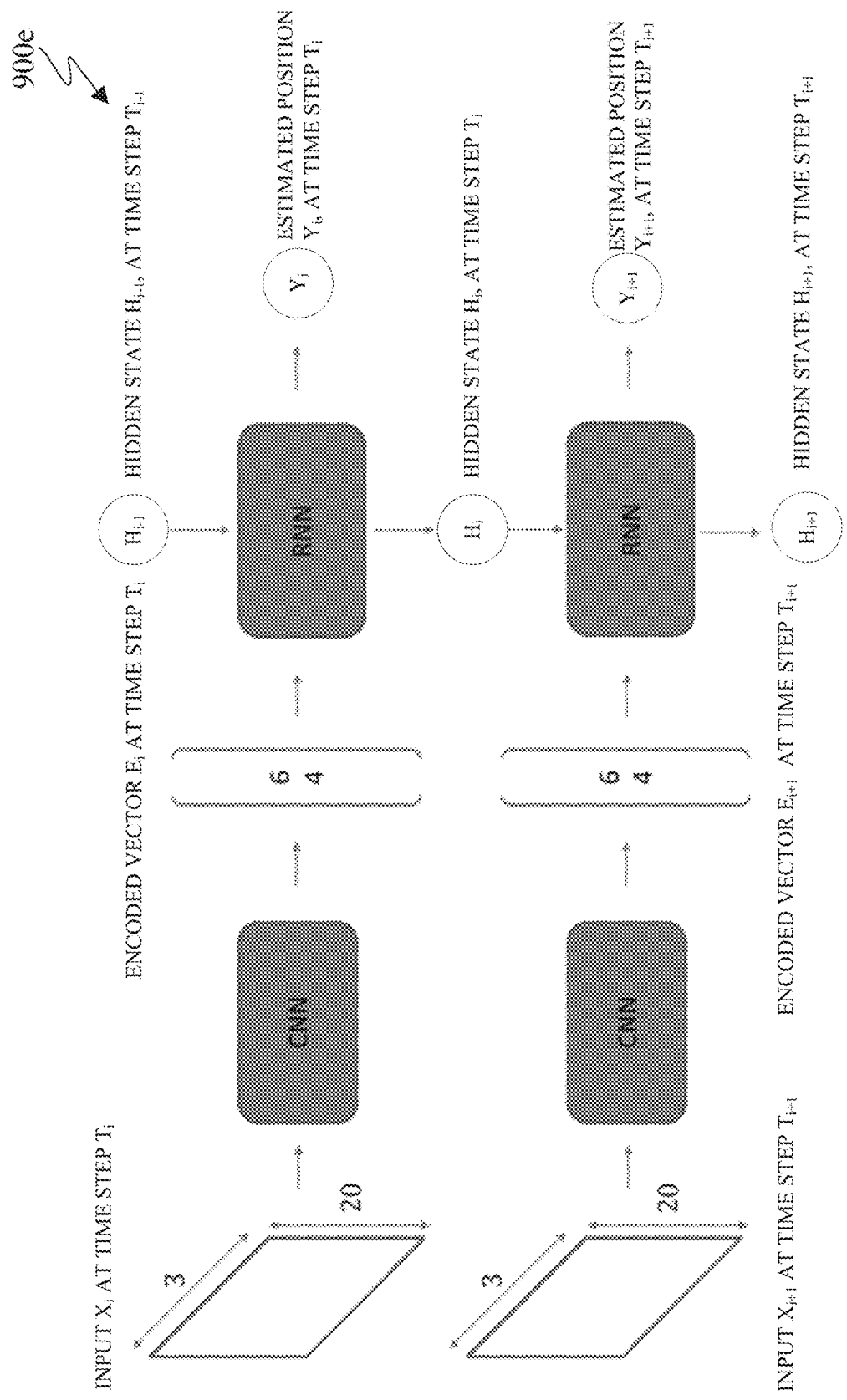

FIGS. 9A-9E illustrate example embodiments of the computational engine 900, of FIG. 6A in accordance with an embodiment of this disclosure. For example, FIG. 9A illustrates an embodiment of an example computational engine 900a in accordance with an embodiment of this disclosure. FIG. 9B illustrates an embodiment of an example computational engine 900b with a pooling layer in accordance with an embodiment of this disclosure. FIG. 9C illustrates an embodiment of example application 900c of the pooling layer of FIG. 9B in accordance with an embodiment of this disclosure. FIGS. 9D and 9E illustrate embodiments of example computational engines 900d and 900e, respectively, in accordance with an embodiment of this disclosure. Although FIGS. 9A-9E illustrates example computation engines various changes can be made to FIGS. 9A-9E. For example, while various embodiments are shown as a series of steps, various steps could overlap, occur in parallel, or occur multiple times.

FIG. 9A illustrates computational engine 900a which is similar to the computational engine 900 of FIG. 6A. The computational engine 900a is a Convolutional Neural Network (CNN) which is a type of Artificial Neural Network (ANN). The computational engine 900a is able to learn and recognize a gesture from a received input. The computational engine 900a can include one or more convolutional layers, and an activation function such as a ReLu, Max/Average pooling. The CNN can include a fully connected layer and a Softmax layer for generating a probability of the classes, such as the probability indicates the likely that particular input signal corresponds to a particular gesture.

FIG. 9B illustrates the computational engine 900b which is similar to the computational engine 900 of FIG. 6A and the computational engine 900a of FIG. 9A. The computational engine 900b includes a pooling layer that can increase the recognition rate as well as stabilize the output when there are invariant shifts to the input. The pooling layer of FIG. 9B can be a Gaussian pooling layer. FIG. 9C illustrates an embodiment of example application 900c of an average Gaussian pooling layer of the computational engine 900b. As shown in the example application 900c, the Gaussian pooling layer is based on a filter size of 3, standard deviation (σ) of 1.0, and a stride of 1. It is noted that other parameters can be used for a Gaussian pooling layer.

The Gaussian pooling layer can blur and then down sample the input. First a filter will be selected based on parameters such as a filter size, s, and a standard deviation, σ. The kernel coefficients are identified using a Gaussian function as described in Equation (20), below. In Equation (20), x is the horizontal direction $x \in [-s, s]$, $x \in \mathbb{N}$.

$$K(x, y) = \frac{1}{2\pi\sigma^2} e^{-\frac{x^2+y^2}{2\sigma^2}} \quad (20)$$

The filter slides across the input matrix by a certain number of strides at a time to perform pixel-wise multiplication. In certain embodiments, the certain number corresponds number of pixels shifts over the input matrix. FIG. 9C illustrates an example result from the pixel wise multiplication. In certain embodiments, the average result from the pixel wise multiplication is identified. In other embodiments, maximum of the result is identified. In yet other embodiments, the minimum of the result will be is identified.

Embodiments of the present disclosure take into consideration that the benefit of using the Gaussian Pooling layer is to ensure the robustness of the ANN toward invariant shifts as well as boosting its performance. For example, the performance of the ANN is increased and the accuracy in recognizing the correct label is increased significantly against invariant shift cases. Additionally, using the Pooling layer enables the computational engine to input collect from different sensor platforms while still identifying the gesture from the input signal.

FIG. 9D illustrates the computational engine 900d which is similar to the computational engine 900 of FIG. 6A. FIG. 9E illustrates the computational engine 900e which is similar to the computational engine 900 of FIG. 6A. The computational engines 900d and 900e are a Convolutional Recurrent Neural Network (ConvRNN). ConvRNN is a type of Artificial Neural Network (ANN) that combines CNN and Recurrent Neural Network (RNN). An RNN is a type of Artificial Neural Network (ANN) that handle time sequence data.

The ConvRNN as shown in FIGS. 9D and 9E include a two components. The first component extracts special relations from the RDM two-dimensional input (as generated by the RDM generator 812 of FIG. 8B). The second component includes a long-short-term memory (LSTM) which is a type of RNN that deals with long time-series sequences. Using an LSTM enables the computational engine 900d to learn the temporal relation between each data frame in the time series. The purpose of using the LSTM is to learn the temporal relation between each data frame in the time series. The LSTM can identify a pattern in the temporal domain. The LSTM is designed to avoid a long-term dependency problem. Together the first component and the second component, learn the pattern in the spatial and temporal domain from the input data, thereafter a fully connected layer is used to recognize non-linear patterns from the feature vector extracted from the previous components in order to generate the tracking information for identifying the gesture.

For example, as shown in FIG. 9E, at time step ti, the pre-processed input $x_i$ (as generated by the signal processing engine 800) is input into the ANN. The convolutional component of the ANN (such as the CNN) extracts spatial information from the input $x_i$ and generates an encoded vector et. The encoded vector et is then inputted into the recurrent component of the ANN (such as the RNN). The recurrent component of the ANN uses the encoded vector et and the hidden state from the previous time step, $h_{t-1}$, to identify tracking information $y_i$. It is noted that if there is no previous time step, then the input $h_{i-1}$ is blank. The hidden state h is a feature vector that includes the memory of the ANN.

Although FIGS. 9A through 9E illustrate example methods and diagrams, various changes may be made to FIGS. 9A through 9E. For example, components of the computational engines may be omitted or replaced with other components.

Figure 10:
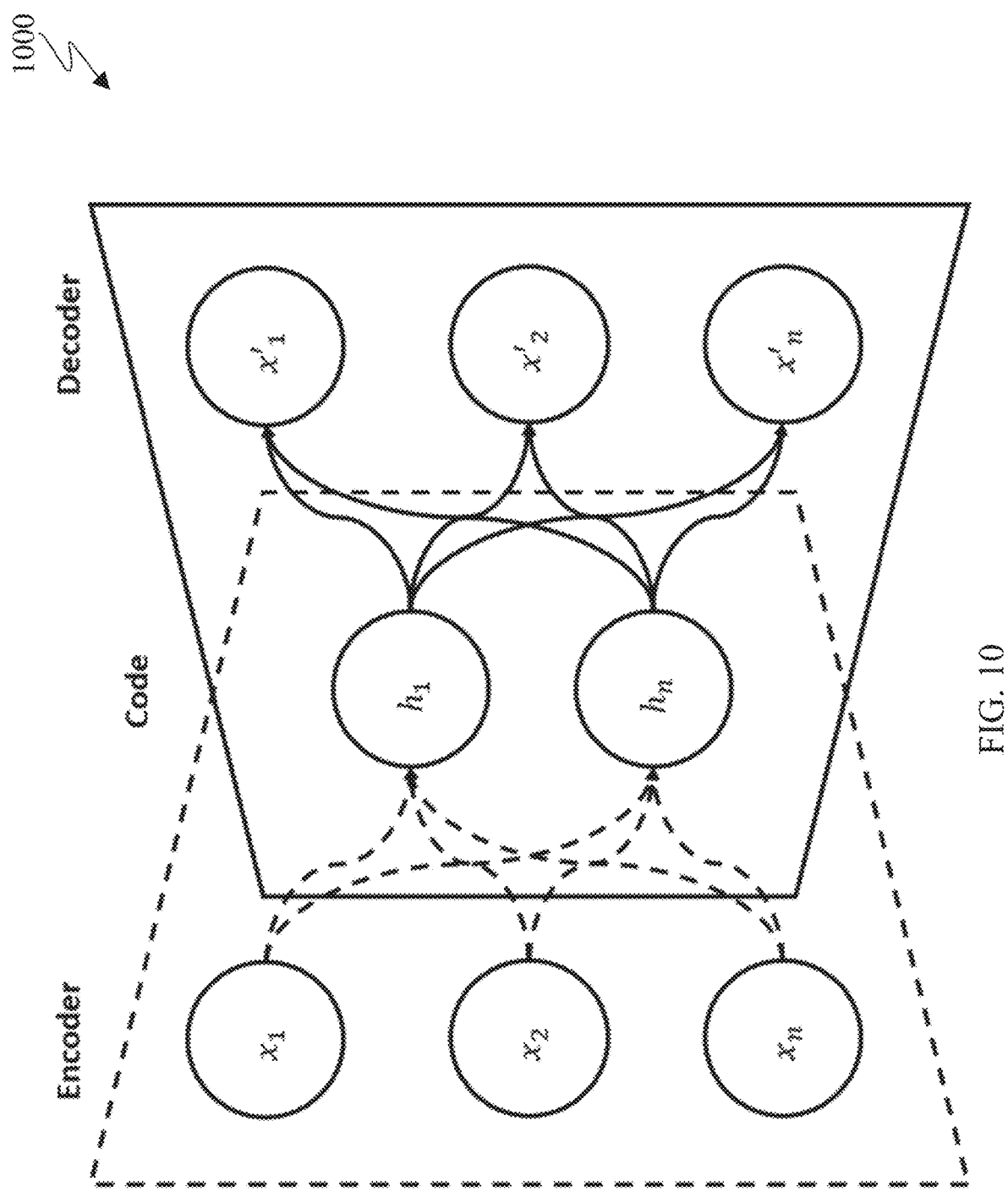
FIG. 10 illustrates an auto-encoder in accordance with an embodiment of this disclosure.

FIG. 10 illustrates an auto-encoder 1000 in accordance with an embodiment of this disclosure. The embodiment of the auto-encoder 1000 is for illustration only. Other embodiments can be used without departing from the scope of the present disclosure.

As shown in FIG. 10, the auto-encoder 1000 can be performed by any one of the client device 106-114 of FIG. 1, the electronic device 400 of FIG. 4A the electronic device 502 of FIG. 5 and can include internal components similar to that of electronic device 200 of FIG. 2 and the electronic device 301 of FIG. 3. However, the auto-encoder 1000 as shown in FIG. 10 could be used with any other suitable electronic device and in any suitable system, such as when performed by the electronic device 200.

An auto-encoder is special type of ANN that can be used to learn efficiently encode data in a supervised or unsupervised manner. In certain embodiments, the auto-encoder 1000 could be included as a component of the signal processing engine 800 of FIG. 6A. Using an auto-encoder, such as the auto-encoder 1000 can increase performance and reduce the computational burden in the computational engine 900 of FIG. 6A. For example, the auto-encoder 1000 can reduce redundant information in the input as well as boost the transferability of the data.

The auto-encoder 1000 can encoder the input, denoise the input, or a combination there of. For example, if the auto-encoder 1000 is used to denoise the data input, the whole ANN could be used to produce the denoised data $[x_1', x_2', \ldots, x_n']$. Alternatively, if the auto-encoder 1000 is used to encode the data input, only the Encoder part of the ANN should be used to produce the encoded data $[h_1, \ldots, h_n]$.

In certain embodiments, the auto-encoder 1000 is used to reduce the noise level from the clipped TVD. Using the auto-encoder 1000 to reduce noise level from the clipped TVD refines the input by applying anti-aliasing like effect on the input data. The denoised data is later used in the computational engine 900 of FIG. 6A to train and classify to recognize the correct gesture. The auto-encoder 1000 will attempt to randomly corrupting some of the input values by introducing noises and then try to reconstruct the data, since an auto-encoder is able to reconstruct data from limited information. The reconstructed data will be imperfect comparing to the original data which effectively remove most of the noises in the original data. Using this denoised data for the computational engine 900 of FIG. 6A improves the performance with the recognition tasks.

Although FIG. 10 illustrates an example auto-encoder 1000, various changes may be made to FIG. 10. For example, more or less inputs can be provided to the auto-encoder 1000.

Figure 11:
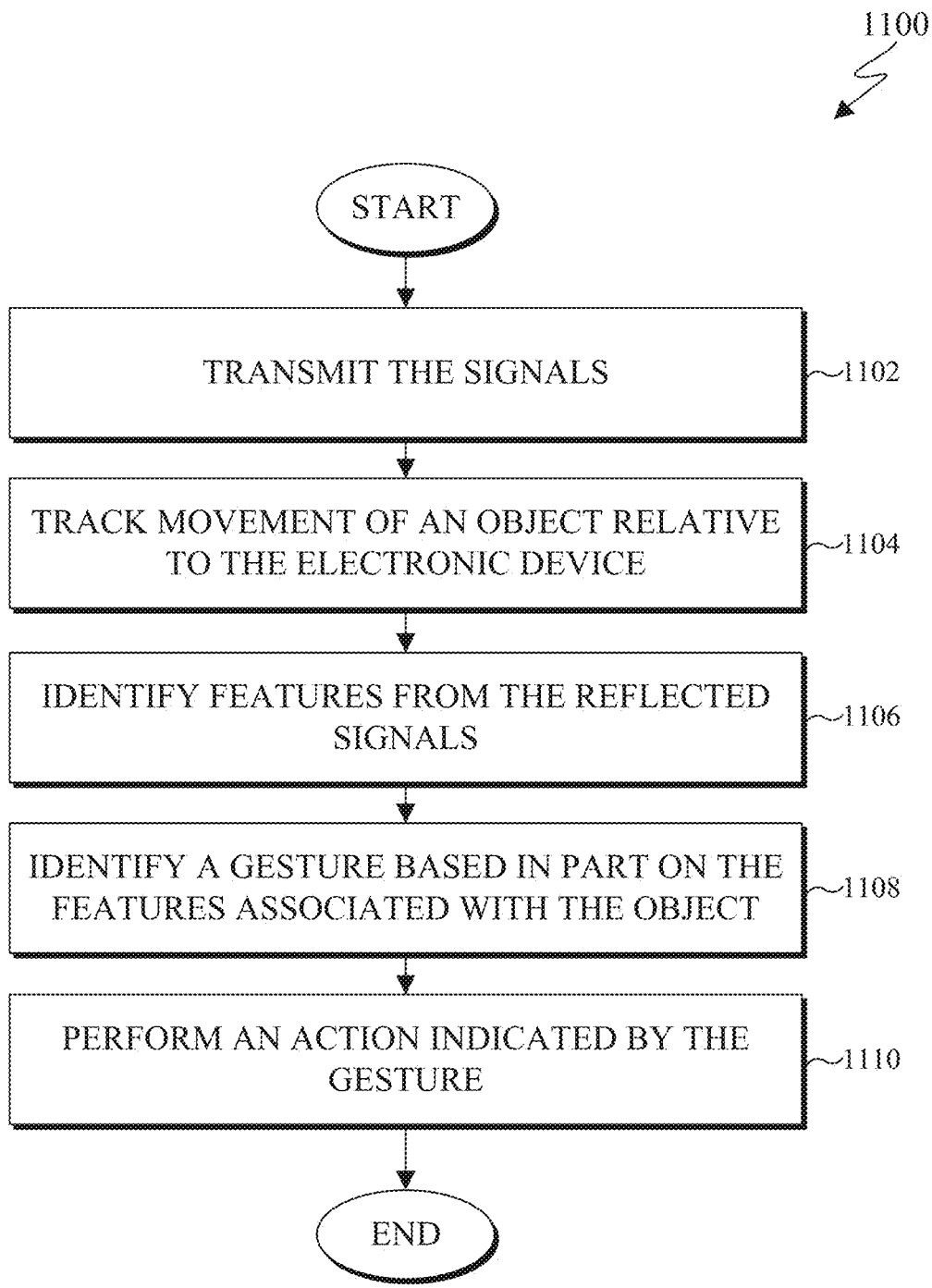
FIG. 11 illustrates a flowchart for gesture recognition in accordance with an embodiment of this disclosure.

FIG. 11 illustrates an example method 1100 for gesture recognition according to embodiments of this disclosure. The method 1100 is described as implemented by any one of the client device 106-114 of FIG. 1, the electronic device 400 of FIG. 4A the electronic device 502 of FIG. 5 and can include internal components similar to that of electronic device 200 of FIG. 2 and the electronic device 301 of FIG. 3. However, the method 1100 as shown in FIG. 11 could be used with any other suitable electronic device and in any suitable system, such as when performed by the electronic device 200.

In step 1102, the electronic device 200 emits signals. The electronic device 200 can also receive the transmitted signals that reflected off of a target object via a radar transceiver, such as the measuring transceiver 270 of FIG. 2. In certain embodiments, the signals are radar signals. In other embodiments, the signals are ultrasonic signals or the like.

In response to determination that a triggering event occurred, in step 1104, the electronic device 200 tracks movement of an object based on the received signals that reflect off of the object. The electronic device 200 can track the movement of the object relative to the electronic device 200. In certain embodiments, the electronic device 200 can track the movement of the object within a region of interest based on the reflections of the received signals. The electronic device can identify range measurements and speed measurements associated with the object based on the reflected signals.

In certain embodiments, the electronic device 200 detects one or more triggering events. The triggering event is an event that triggers the gesture recognition process. For example, electronic device 200 can detect an input associated with a predefined location on the electronic device 200. Upon detecting the input, the electronic device 200 determines whether the input corresponds to a triggering event. The determination can be based on the location of the input, type of input, or the like. In certain embodiments, in response to detecting the input the electronic device 200 transmits the signals of step 1102. In other embodiments, the detected input that corresponds to the triggering event is a gesture that is detected using the transmitted signals of step 1102.

In step 1106, the electronic device 200 identifies features from the reflected signals. The features are used for classifying a gesture associated with the object. The features include one or more of range feature, velocity/Doppler feature, RDM feature, TVD, angle feature, and micro Doppler feature of a moving human body part. In certain embodiments, only one or some of the features may be needed to identify a particular gesture.

In certain embodiments, before the electronic device 200 identifies the features, the electronic device 200 identifies a compensation coefficient associated with a delay tap. The compensation coefficient represents variations in the CIR. The electronic device 200 can then modify the reflected signals to compensate for the changes associated with the CIR. For example, the electronic device 200 modifies the reflected signals using the compensation coefficient. The electronic device 200 then identifies the features from the modified reflected signals.

In certain embodiments, to identify the features, the electronic device 200 generates a RDM that represents the reflected signal in two dimensions. Since the reflected signals can represent a data frame that includes multiple dimensions, such as a burst dimension, a channel dimension, and a tap dimension, the electronic device 200 modifies the data frame to reduce the data frame to a two-dimensional representation. To generate the RDM, the electronic device 200 removes a zero doppler value from the burst dimension of the data frame. The electronic device 200 also applies a Fast Fourier Transform to the burst dimension. The electronic device 200 converts the reflected signals included in the data frame to a decibel scale. The electronic device 200 also removes a certain number of taps from the tap dimension. Thereafter the electronic device 200 averages the data frame over the channel dimension to generate the RDM in two-dimensions.

In step 1108, the electronic device 200 identifies a gesture based in part on the identified features from the reflected signals. That is, after the electronic device 200 identifies the features, the electronic device processes the data in order to identify the gesture represented by the reflected signals. For example, the electronic device 200 generates a clipped map by removing a portion of the identifies features. To generate the clipped map the electronic device 200 can identify an upper threshold and a lower threshold from a TVD. The TVD indicates the radial velocity between the electronic device and the object that is moving. The electronic device 200 can then generate a threshold window based on both the upper and lower thresholds. A portion of the identified features are removed based on the threshold window indicating the region of interest and noise removal.

The electronic device 200 can also normalize the clipped map. In certain embodiments, the electronic device 200 also refines the normalized clipped map by applying a low pass filter for noise removal.

After the clipped map is normalized or refined, the electronic device 200 identifies the gesture using a neural network. In certain embodiments, the neural network includes a Gaussian pooling layer that blurs and down samples the reflected signals represented by the clipped map. In certain embodiments, the neural network can include a CNN and an RNN. The CNN extracts spatial relationships from the reflected signals represented by the clipped map and the RNN identifies temporal relationships from the reflected signals represented by the clipped map.

In step 1110, the electronic device 200 performs an action based on the identified gesture. For example, based on the detected input, the electronic device 200 can change the brightness of the display or the volume of sound that is output through a speaker. In certain embodiments, the triggering event can also indicate a particular action that an identified gesture represents. For example, if the triggering event occurs when the electronic device 200 receives a phone call, and the gesture is a wave of a hand of the user, the action could be to answer the phone call. However if the triggering event is an input of a button on the electronic device 200, then the detected wave gesture could correspond to a different indicated action.

Although FIG. 11 illustrates example methods, various changes may be made to FIG. 11. For example, while the method 1100 is shown as a series of steps, various steps could overlap, occur in parallel, occur in a different order, or occur multiple times. In another example, steps may be omitted or replaced by other steps.

The above flowcharts illustrate example methods that can be implemented in accordance with the principles of the present disclosure and various changes could be made to the methods illustrated in the flowcharts herein. For example, while shown as a series of steps, various steps in each figure could overlap, occur in parallel, occur in a different order, or occur multiple times. In another example, steps may be omitted or replaced by other steps.

Although the figures illustrate different examples of user equipment, various changes may be made to the figures. For example, the user equipment can include any number of each component in any suitable arrangement. In general, the figures do not limit the scope of this disclosure to any particular configuration(s). Moreover, while figures illustrate operational environments in which various user equipment features disclosed in this patent document can be used, these features can be used in any other suitable system. None of the description in this application should be read as implying that any particular element, step, or function is an essential element that must be included in the claims scope.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An electronic device for gesture recognition, the electronic device comprising:
   a transceiver configured to transmit and receive signals for measuring range and speed; and
   a processor operably connected to the transceiver and configured to:
   transmit the signals, via the transceiver,
   in response to a determination that a triggering event occurred, track movement of an object relative to the electronic device within a region of interest based on reflections of the signals received by the transceiver to identify range measurements and speed measurements associated with the object,
   identify features from the reflected signals, based on at least one of the range measurements and the speed measurements,
   perform an adaptive thresholding to remove a portion of the identified features,
   identify a gesture based in part on a portion of the features that were not removed from the reflected signals, and
   perform an action indicated by the gesture.

2. The electronic device of claim 1, the processor is further configured to:
   determine whether the triggering event occurred based on a detection of: (i) a gesture including at least one repetition in a feature domain, (ii) a physical touching of the electronic device, or (iii) a connection to another device; and
   transmit, via the transceiver, signature signals to identify the region of interest associated with the movement of the object.

3. The electronic device of claim 1, wherein to identify the gesture, the processor is configured to:
   perform the adaptive thresholding to generate a clipped map;
   normalize the clipped map; and
   identify the gesture from the normalized map.

4. The electronic device of claim 3, wherein to perform the adaptive thresholding, the processor is configured to:
   identify an upper threshold and a lower threshold from the identified features in a time velocity diagram (TVD), wherein the TVD is represented as a one dimensional array and indicates a radial velocity between the transceiver and the object that is moving;
   generate a threshold window based on the upper threshold and the lower threshold; and
   remove the portion of the identified features based on the threshold window to generate the clipped map, wherein the clipped map corresponds to the region of interest of the identified features,
   wherein the adaptive thresholding removes noise from the reflected signals.

5. The electronic device of claim 3, wherein the processor is further configured to apply a low pass filter to remove noise from the normalized map.

6. The electronic device of claim 1, wherein the processor is further configured to:
   identify a compensation coefficient associated with a delay tap, the compensation coefficient represents variations in a channel impulse response (CIR);
   modify the reflected signals to compensate for changes associated with the CIR based on the compensation coefficient; and
   identify the features from the modified reflected signals.

7. The electronic device of claim 1, wherein:
   the reflected signals represent a data frame including a burst dimension, a channel dimension, a repetition dimension, and a tap dimension, and
   to identify the features from the reflected signals, the processor is further configured to generate a range Doppler map (RDM) representing the reflected signals in two dimensions.

8. The electronic device of claim 7, wherein to generate the RDM, the processor is configured to:
   remove a zero doppler value from the burst dimension of the data frame;
   apply a Fast Fourier Transform to the burst dimension;
   convert the reflected signals included in the data frame to a decibel scale;
   remove a first tap and a second tap from the tap dimension;
   extract a portion of bursts along the burst dimension; and
   average the data frame over the channel dimension to generate the RDM in two-dimensions,
   wherein the RDM is based in part on the portion of bursts along the burst dimension and remaining taps after the first tap and the second tap are removed.

9. The electronic device of claim 1, further comprising a neural network that includes a Gaussian pooling layer,
   wherein the Gaussian Pooling layer is configured to blur and down-sample the reflected signals associated with the object, and
   wherein the processor is further configured to identify the gesture using the neural network based on the blurred and down-sampled reflected signals.

10. The electronic device of claim 1, further comprising convolutional recurrent neural network that includes a convolutional neural network and recurrent neural network,
    wherein the convolutional neural network is configured to extract spatial relationships from a RDM representing the reflected signals in two dimensions,
    wherein the recurrent neural network is configured to identify temporal relationships between the reflected signals in a time series, and wherein the processor is further configured to identify the gesture, based on the extracted spatial relationships and the identified temporal relationships.

11. A method for gesture recognition, the method comprising:
   transmitting signals, via a transceiver;
   in response to a determination that a triggering event occurred, tracking movement of an object relative to an electronic device within a region of interest based on reflections of the signals received by the transceiver to identify range measurements and speed measurements associated with the object;
   identifying features from the reflected signals, based on at least one of the range measurements and the speed measurements;
   performing an adaptive thresholding to remove a portion of the identified features
   identifying a gesture based in part on a portion of the features that were not removed from the reflected signals; and
   performing an action indicated by the gesture.

12. The method of claim 11, further comprising:
   determine whether the triggering event occurred based on a detection of: (i) a gesture including at least one repetition in a feature domain, (ii) a physical touching of the electronic device, or (iii) a connection to another device; and
   transmitting, via the transceiver, signature signals to identify the region of interest associated with the movement of the object.

13. The method of claim 11, wherein identifying the gesture comprises:
   performing the adaptive thresholding to generate a clipped map;
   normalizing the clipped map; and
   identifying the gesture from the normalized map.

14. The method of claim 13, wherein performing the adaptive thresholding comprises:
   identifying an upper threshold and a lower threshold from the identified features in a time velocity diagram (TVD), wherein the TVD is represented as a one dimensional array and indicates a radial velocity between the transceiver and the object that is moving;
   generating a threshold window based on the upper threshold and the lower threshold; and
   removing the portion of the identified features based on the threshold window to generate the clipped map, wherein the clipped map corresponds to the region of interest of the identified features,
   wherein the adaptive thresholding removes noise from the reflected signals.

15. The method of claim 13, further comprising applying a low pass filter to remove noise from the normalized map.

16. The method of claim 11, further comprising:
   identifying a compensation coefficient associated with a delay tap, the compensation coefficient represents variations in a channel impulse response (CIR);
   modifying the reflected signals to compensate for changes associated with the CIR based on the compensation coefficient; and
   identifying the features from the modified reflected signals.

17. The method of claim 11, wherein:
   the reflected signals represent a data frame including a burst dimension, a channel dimension, a repetition dimension, and a tap dimension, and
   identifying the features from the reflected signals, comprises generating a range Doppler map (RDM) representing the reflected signals in two dimensions.

18. The method of claim 17, wherein generating the RDM, comprises:
   removing a zero doppler value from the burst dimension of the data frame;
   applying a Fast Fourier Transform to the burst dimension;
   converting the reflected signals included in the data frame to a decibel scale;
   removing a first tap and a second tap from the tap dimension, wherein the first tap is an initial tap in the tap dimension and the second tap is a last tap in the tap dimension;
   extracting a portion of bursts along the burst dimension; and
   averaging the data frame over the channel dimension to generate the RDM in two-dimensions,
   wherein the RDM is based in part on the portion of bursts along the burst dimension and remaining taps after the first tap and the second tap are removed.

19. The method of claim 11, further comprising:
   blurring and down-sampling the reflected signals associated with the object using a neural network that includes a Gaussian pooling layer, and
   identifying the gesture using the neural network based on the blurred and down-sampled reflected signals.

20. The method of claim 11, further comprising:
   extracting spatial relationships from a RDM representing the reflected signals in two dimensions, using a convolutional neural network;
   identifying temporal relationships between the reflected signals in a time series using a recurrent neural network; and
   identifying the gesture, based on the extracted spatial relationships and the identified temporal relationships.

21. A non-transitory computer readable medium embodying a computer program, the computer program comprising computer readable program code that, when executed by a processor of an electronic device, causes the processor to:
   transmit signals, via a transceiver;
   in response to a determination that a triggering event occurred, track movement of an object relative to the electronic device within a region of interest based on reflections of the signals received by the transceiver to identify range measurements and speed measurements associated with the object;
   identify features from the reflected signals, based on at least one of the range measurements and the speed measurements;
   perform an adaptive thresholding to remove a portion of the identified features;
   identify a gesture based in part on a portion of the features that were not removed from the reflected signals; and
   perform an action indicated by the gesture.

22. The non-transitory computer readable medium of claim 21, wherein the computer readable program code, when executed by the processor, further causes the processor to:
   perform the adaptive thresholding to generate a clipped map;
   normalize the clipped map; and
   identify the gesture from the normalized map.

23. The non-transitory computer readable medium of claim 22, wherein the computer readable program code, when executed by the processor, further causes the processor to:
- identify an upper threshold and a lower threshold from the identified features in a time velocity diagram (TVD), wherein the TVD is represented as a one dimensional array and indicates a radial velocity between the transceiver and the object that is moving;
- generate a threshold window based on the upper threshold and the lower threshold; and
- remove the portion of the identified features based on the threshold window to generate the clipped map, wherein the clipped map corresponds to the region of interest of the identified features,
- wherein the adaptive thresholding removes noise from the reflected signals.

24. The non-transitory computer readable medium of claim 21, wherein the computer readable program code, when executed by the processor, further causes the processor to:
- identify a compensation coefficient associated with a delay tap, the compensation coefficient represents variations in a channel impulse response (CIR);
- modify the reflected signals to compensate for changes associated with the CIR based on the compensation coefficient; and
- identify the features from the modified reflected signals.

25. The non-transitory computer readable medium of claim 21, wherein the computer readable program code, when executed by the processor, further causes the processor to generate a range Doppler map (RDM) representing the reflected signals in two dimensions.

* * * * *